(12) United States Patent
Lorenz et al.

(10) Patent No.: US 11,795,500 B2
(45) Date of Patent: Oct. 24, 2023

(54) METHODS FOR DETECTING RNA BINDING PROTEIN COMPLEXES

(71) Applicant: Eclipse Bioinnovations, Inc., San Diego, CA (US)

(72) Inventors: Daniel A. Lorenz, San Diego, CA (US); Karen B. Chapman, San Diego, CA (US)

(73) Assignee: Eclipse Bioinnovations, Inc., San Diego, CA (US)

( * ) Notice: Subject to any disclaimer, the term of this patent is extended or adjusted under 35 U.S.C. 154(b) by 0 days.

(21) Appl. No.: 17/820,735

(22) Filed: Aug. 18, 2022

(65) Prior Publication Data
US 2023/0126137 A1    Apr. 27, 2023

Related U.S. Application Data

(60) Provisional application No. 63/295,296, filed on Dec. 30, 2021, provisional application No. 63/235,070, filed on Aug. 19, 2021.

(51) Int. Cl.
*C12Q 1/68* (2018.01)
*C12Q 1/6851* (2018.01)
*C12N 15/10* (2006.01)
*C12Q 1/6804* (2018.01)

(52) U.S. Cl.
CPC .......... *C12Q 1/6851* (2013.01); *C12N 15/1065* (2013.01); *C12N 15/1096* (2013.01); *C12Q 1/6804* (2013.01)

(58) Field of Classification Search
CPC ..................................................... C12Q 1/68
USPC ........................................................ 435/6.1
See application file for complete search history.

(56) References Cited

U.S. PATENT DOCUMENTS

| 9,902,950 B2 | 2/2018 | Church et al. |
| 10,655,162 B1* | 5/2020 | Goren et al. ....... G01N 33/6878 |

(Continued)

FOREIGN PATENT DOCUMENTS

| WO | 2013053742 A1 | 4/2013 |
| WO | 2019070638 A1 | 4/2019 |

(Continued)

OTHER PUBLICATIONS

Mugisha, "Identifying the RNA targets of RNA binding proteins with clip" 84-92. Methods, Web. Nov. 1, 2020, Entire Document; doi: 10.1016/j.ymeth.2019.11.011.

Grosswendt et al., Unambiguous Identification of miRNA:Target Site Interactions by Different Types of Ligation Reactions, Molecular Cell, Jun. 19, 2014 (19,06.2014), Vol. 54, Iss. 6, Pgs. 1042-1054. Entire Document.

(Continued)

*Primary Examiner* — Aaron A Priest
(74) *Attorney, Agent, or Firm* — Knobbe, Martens, Olson & Bear, LLP

(57) ABSTRACT

The present disclosure relates to methods of identifying RNA targets of RNA binding proteins. In aspects, the disclosure relates to a method of identifying RNA molecules bound by RNA binding proteins. Some embodiments of the present disclosure relate to a method that can definitively identify direct RNA-target interactions with targeted proteins without the requirement for immunoprecipitation or gel extraction. In some embodiments, the method may include combining multiple antibodies in the same sample.

20 Claims, 19 Drawing Sheets

Specification includes a Sequence Listing.

(56) References Cited

U.S. PATENT DOCUMENTS

| | | | |
|---|---|---|---|
| 2013/0029326 A1 | 1/2013 | Jendrisak et al. |
| 2015/0284797 A1 | 10/2015 | Dawson et al. |
| 2018/0371006 A1 | 12/2018 | Kazakov et al. |
| 2019/0144850 A1 | 5/2019 | Kreader |
| 2020/0190574 A1 | 6/2020 | Zhong et al. |
| 2020/0216830 A1 | 7/2020 | Dixon et al. |

FOREIGN PATENT DOCUMENTS

| | | | |
|---|---|---|---|
| WO | 2019078909 A2 | 4/2019 |

OTHER PUBLICATIONS

International Search Report and Written Opinion received in PCT Application No. PCT/US2022/075122 (EBIO.005WO) as mailed Jan. 25, 2023 in 40 pages.

Jung et al, Quantifying RNA-protein interactions in situ using modified-MTRIPs and proximity ligation, Nucleic Acids Res. Jan. 7, 2013;41(1):e12. doi: 10.1093/nar/gks837. Epub Sep. 4, 2012.*

Lorenz, "Multiplexed transcriptome discovery of RNA binding protein binding sites by antibody-barcode eCLiP". bioRxiv. Web. Jun. 8, 2022; Entire Document; doi: 10.1101/2022.06.08.495357.

Shahi et al., Abseq: Ultrahigh-throughput single cell protein profiling with droplet microfluidic barcoding, Scientific Reports, Web. Mar. 14, 2017, Entire Document; doi: 10.1038/srep44447.

Van Nostrand et al., Robust transcriptome-wide discovery of RNA binding protein binding sites with enhanced CLIP (eCLIP), HHS Public Access, Sep. 28, 2016, Pgs. 1-19.

Zhang et al, A proximity-dependent assay for specific RNA-protein interactions in intact cells, RNA. Nov. 2016; 22(11): 1785-1792. doi: 10.1261/rna.058248.116.*

\* cited by examiner

| Oligo Type | Top Motif | Number of Sites |
|---|---|---|
| DNA | UGCAUGCG | 3732 |
| RNA | GGUGCAUG | 3305 |

FIG. 3

| qPCR Target | bc3 - 65C | bc6 - 65C | bc7 - 65C |
|---|---|---|---|
| BC1 | 19.8 | 20.0 | 19.4 |
| BC2 | 18.9 | 19.6 | 19.2 |
| BC3 | 20.7 | 23.6 | 23.1 |
| BC4 | 19.4 | 19.4 | 19.2 |
| BC5 | 20.3 | 20.3 | 19.4 |
| BC6 | 21.8 | 19.3 | 21.1 |
| BC7 | 21.9 | 22.0 | 20.1 |
| BC8 | 18.9 | 19.4 | 18.8 |
| BC9 | 21.1 | 20.7 | 20.1 |
| BC10 | 20.7 | 20.8 | 20.0 |
| qpcr | 16.9 | 17.0 | 16.5 |

FIG. 11

```
                              SEQUENCE LISTING

Sequence total quantity: 44
SEQ ID NO: 1           moltype = DNA  length = 36
FEATURE                Location/Qualifiers
source                 1..36
                       mol_type = other DNA
                       organism = synthetic construct
SEQ ID NO: 1
attactcgnn nnnnnnagat cggaagagcg tcgtgt                                    36

SEQ ID NO: 2           moltype = DNA  length = 36
FEATURE                Location/Qualifiers
source                 1..36
                       mol_type = other DNA
                       organism = synthetic construct
SEQ ID NO: 2
tccggagann nnnnnnagat cggaagagcg tcgtgt                                    36

SEQ ID NO: 3           moltype = DNA  length = 36
FEATURE                Location/Qualifiers
source                 1..36
                       mol_type = other DNA
                       organism = synthetic construct
SEQ ID NO: 3
cgctcattnn nnnnnnagat cggaagagcg tcgtgt                                    36

SEQ ID NO: 4           moltype = DNA  length = 36
FEATURE                Location/Qualifiers
source                 1..36
                       mol_type = other DNA
                       organism = synthetic construct
SEQ ID NO: 4
gagattccnn nnnnnnagat cggaagagcg tcgtgt                                    36

SEQ ID NO: 5           moltype = DNA  length = 36
FEATURE                Location/Qualifiers
source                 1..36
                       mol_type = other DNA
                       organism = synthetic construct
SEQ ID NO: 5
attcagaann nnnnnnagat cggaagagcg tcgtgt                                    36
```

```
SEQ ID NO: 6              moltype = DNA   length = 35
FEATURE                   Location/Qualifiers
source                    1..35
                          mol_type = other DNA
                          organism = synthetic construct
SEQ ID NO: 6
gattcgtnnn nnnnnagatc ggaagagcgt cgtgt                              35

SEQ ID NO: 7              moltype = DNA   length = 36
FEATURE                   Location/Qualifiers
source                    1..36
                          mol_type = other DNA
                          organism = synthetic construct
SEQ ID NO: 7
ctgaagctnn nnnnnnagat cggaagagcg tcgtgt                             36

SEQ ID NO: 8              moltype = DNA   length = 36
FEATURE                   Location/Qualifiers
source                    1..36
                          mol_type = other DNA
                          organism = synthetic construct
SEQ ID NO: 8
taatgcgcnn nnnnnnagat cggaagagcg tcgtgt                             36

SEQ ID NO: 9              moltype = DNA   length = 36
FEATURE                   Location/Qualifiers
source                    1..36
                          mol_type = other DNA
                          organism = synthetic construct
SEQ ID NO: 9
cggctatgnn nnnnnnagat cggaagagcg tcgtgt                             36

SEQ ID NO: 10             moltype = DNA   length = 36
FEATURE                   Location/Qualifiers
source                    1..36
                          mol_type = other DNA
                          organism = synthetic construct
SEQ ID NO: 10
tccgcgaann nnnnnnagat cggaagagcg tcgtgt                             36

SEQ ID NO: 11             moltype = DNA   length = 15
FEATURE                   Location/Qualifiers
source                    1..15
                          mol_type = other DNA
                          organism = synthetic construct
SEQ ID NO: 11
acacgacgct cttcc                                                    15

SEQ ID NO: 12             moltype = DNA   length = 22
FEATURE                   Location/Qualifiers
source                    1..22
                          mol_type = other DNA
                          organism = synthetic construct
SEQ ID NO: 12
agatcggaag agcacacgtc tg                                            22

SEQ ID NO: 13             moltype = DNA   length = 70
FEATURE                   Location/Qualifiers
source                    1..70
                          mol_type = other DNA
                          organism = synthetic construct
SEQ ID NO: 13
aatgatacgg cgaccaccga gatctacact atagcctaca ctctttccct acacgacgct   60
cttccgatct                                                          70

SEQ ID NO: 14             moltype = DNA   length = 66
FEATURE                   Location/Qualifiers
source                    1..66
                          mol_type = other DNA
                          organism = synthetic construct
SEQ ID NO: 14
```

```
                                      -continued
caagcagaag acggcatacg agatcgagta atgtgactgg agttcagacg tgtgctcttc   60
cgatct                                                              66

SEQ ID NO: 15           moltype = DNA   length = 15
FEATURE                 Location/Qualifiers
source                  1..15
                        mol_type = other DNA
                        organism = synthetic construct
SEQ ID NO: 15
acacgacgct cttcc                                                    15

SEQ ID NO: 16           moltype = DNA   length = 22
FEATURE                 Location/Qualifiers
source                  1..22
                        mol_type = other DNA
                        organism = synthetic construct
SEQ ID NO: 16
agatcggaag agcacacgtc tg                                            22

SEQ ID NO: 17           moltype = DNA   length = 36
FEATURE                 Location/Qualifiers
source                  1..36
                        mol_type = other DNA
                        organism = synthetic construct
SEQ ID NO: 17
attactcgnn nnnnnnagat cggaagagcg tcgtgt                             36

SEQ ID NO: 18           moltype = DNA   length = 30
FEATURE                 Location/Qualifiers
source                  1..30
                        mol_type = other DNA
                        organism = synthetic construct
SEQ ID NO: 18
nnnnnatcac agatcggaag agcgtcgtgt                                    30

SEQ ID NO: 19           moltype = DNA   length = 30
FEATURE                 Location/Qualifiers
source                  1..30
                        mol_type = other DNA
                        organism = synthetic construct
SEQ ID NO: 19
nnnnncgatg agatcggaag agcgtcgtgt                                    30

SEQ ID NO: 20           moltype = DNA   length = 30
FEATURE                 Location/Qualifiers
source                  1..30
                        mol_type = other DNA
                        organism = synthetic construct
SEQ ID NO: 20
nnnnnttagg agatcggaag agcgtcgtgt                                    30

SEQ ID NO: 21           moltype = DNA   length = 30
FEATURE                 Location/Qualifiers
source                  1..30
                        mol_type = other DNA
                        organism = synthetic construct
SEQ ID NO: 21
nnnnntgacc agatcggaag agcgtcgtgt                                    30

SEQ ID NO: 22           moltype = DNA   length = 30
FEATURE                 Location/Qualifiers
source                  1..30
                        mol_type = other DNA
                        organism = synthetic construct
SEQ ID NO: 22
nnnnnacagt agatcggaag agcgtcgtgt                                    30

SEQ ID NO: 23           moltype = DNA   length = 30
FEATURE                 Location/Qualifiers
source                  1..30
                        mol_type = other DNA
                        organism = synthetic construct
```

```
SEQ ID NO: 23
nnnnngccaa agatcggaag agcgtcgtgt                                      30

SEQ ID NO: 24          moltype = DNA   length = 30
FEATURE                Location/Qualifiers
source                 1..30
                       mol_type = other DNA
                       organism = synthetic construct
SEQ ID NO: 24
nnnnncagat agatcggaag agcgtcgtgt                                      30

SEQ ID NO: 25          moltype = DNA   length = 30
FEATURE                Location/Qualifiers
source                 1..30
                       mol_type = other DNA
                       organism = synthetic construct
SEQ ID NO: 25
nnnnnacttg agatcggaag agcgtcgtgt                                      30

SEQ ID NO: 26          moltype = DNA   length = 30
FEATURE                Location/Qualifiers
source                 1..30
                       mol_type = other DNA
                       organism = synthetic construct
SEQ ID NO: 26
nnnnngatca agatcggaag agcgtcgtgt                                      30

SEQ ID NO: 27          moltype = DNA   length = 30
FEATURE                Location/Qualifiers
source                 1..30
                       mol_type = other DNA
                       organism = synthetic construct
SEQ ID NO: 27
nnnnntagct agatcggaag agcgtcgtgt                                      30

SEQ ID NO: 28          moltype = DNA   length = 15
FEATURE                Location/Qualifiers
source                 1..15
                       mol_type = other DNA
                       organism = synthetic construct
SEQ ID NO: 28
acacgacgct cttcc                                                      15

SEQ ID NO: 29          moltype = DNA   length = 22
FEATURE                Location/Qualifiers
source                 1..22
                       mol_type = other DNA
                       organism = synthetic construct
SEQ ID NO: 29
agatcggaag agcacacgtc tg                                              22

SEQ ID NO: 30          moltype = DNA   length = 70
FEATURE                Location/Qualifiers
source                 1..70
                       mol_type = other DNA
                       organism = synthetic construct
SEQ ID NO: 30
aatgatacgg cgaccaccga gatctacact atagcctaca ctctttccct acacgacgct     60
cttccgatct                                                            70

SEQ ID NO: 31          moltype = DNA   length = 66
FEATURE                Location/Qualifiers
source                 1..66
                       mol_type = other DNA
                       organism = synthetic construct
SEQ ID NO: 31
caagcagaag acggcatacg agatcgagta atgtgactgg agttcagacg tgtgctcttc     60
cgatct                                                                66

SEQ ID NO: 32          moltype = DNA   length = 15
FEATURE                Location/Qualifiers
source                 1..15
                       mol_type = other DNA
```

```
                        organism = synthetic construct
SEQ ID NO: 32
acacgacgct cttcc                                                      15

SEQ ID NO: 33           moltype = DNA   length = 22
FEATURE                 Location/Qualifiers
source                  1..22
                        mol_type = other DNA
                        organism = synthetic construct
SEQ ID NO: 33
agatcggaag agcacacgtc tg                                              22

SEQ ID NO: 34           moltype = DNA   length = 25
FEATURE                 Location/Qualifiers
source                  1..25
                        mol_type = other DNA
                        organism = synthetic construct
SEQ ID NO: 34
acacgacgct cttccgatct gtgat                                           25

SEQ ID NO: 35           moltype = DNA   length = 25
FEATURE                 Location/Qualifiers
source                  1..25
                        mol_type = other DNA
                        organism = synthetic construct
SEQ ID NO: 35
acacgacgct cttccgatct catcg                                           25

SEQ ID NO: 36           moltype = DNA   length = 25
FEATURE                 Location/Qualifiers
source                  1..25
                        mol_type = other DNA
                        organism = synthetic construct
SEQ ID NO: 36
acacgacgct cttccgatct cctaa                                           25

SEQ ID NO: 37           moltype = DNA   length = 25
FEATURE                 Location/Qualifiers
source                  1..25
                        mol_type = other DNA
                        organism = synthetic construct
SEQ ID NO: 37
acacgacgct cttccgatct ggtca                                           25

SEQ ID NO: 38           moltype = DNA   length = 25
FEATURE                 Location/Qualifiers
source                  1..25
                        mol_type = other DNA
                        organism = synthetic construct
SEQ ID NO: 38
acacgacgct cttccgatct actgt                                           25

SEQ ID NO: 39           moltype = DNA   length = 25
FEATURE                 Location/Qualifiers
source                  1..25
                        mol_type = other DNA
                        organism = synthetic construct
SEQ ID NO: 39
acacgacgct cttccgatct ttggc                                           25

SEQ ID NO: 40           moltype = DNA   length = 25
FEATURE                 Location/Qualifiers
source                  1..25
                        mol_type = other DNA
                        organism = synthetic construct
SEQ ID NO: 40
acacgacgct cttccgatct atctg                                           25

SEQ ID NO: 41           moltype = DNA   length = 25
FEATURE                 Location/Qualifiers
source                  1..25
                        mol_type = other DNA
                        organism = synthetic construct
```

```
SEQ ID NO: 41
acacgacgct cttccgatct caagt                                      25

SEQ ID NO: 42           moltype = DNA   length = 25
FEATURE                 Location/Qualifiers
source                  1..25
                        mol_type = other DNA
                        organism = synthetic construct
SEQ ID NO: 42
acacgacgct cttccgatct tgatc                                      25

SEQ ID NO: 43           moltype = DNA   length = 25
FEATURE                 Location/Qualifiers
source                  1..25
                        mol_type = other DNA
                        organism = synthetic construct
SEQ ID NO: 43
acacgacgct cttccgatct agcta                                      25

SEQ ID NO: 44           moltype = DNA   length = 22
FEATURE                 Location/Qualifiers
source                  1..22
                        mol_type = other DNA
                        organism = synthetic construct
SEQ ID NO: 44
cagacgtgtg ctcttccgat ct                                         22
```

METHODS FOR DETECTING RNA BINDING PROTEIN COMPLEXES

CROSS REFERENCE TO RELATED APPLICATIONS

This application claims the benefit of U.S. Provisional Application No. 63/235,070 filed on Aug. 19, 2021 and U.S. Provisional Application No. 63/295,296 filed on Dec. 30, 2021, which are incorporated by reference in its entirety.

BACKGROUND

RNA binding proteins (RBPs) are an important class of proteins involved in nearly every aspect of RNA biology, including but not limited to the regulation of RNA stability, localization, and translational efficiency. There are currently thousands of RBPs with many more yet to be identified and characterized. Understanding the function of an RBP largely relies on determining what RNAs it binds. Current methods to characterize these interactions have predominately relied on Cross-Linking followed by Immuno-Precipitation (CLIP) based technologies. While these technologies have been instrumental in the characterization of hundreds of RBPs, the methods are cumbersome and low throughput.

REFERENCE TO SEQUENCE LISTING

The present application is filed with a Sequence Listing in Electronic format. The Sequence Listing is provided as a file entitled EBIO.005WO ST 26.xml, created Aug. 17, 2022, which is approximately 39.3 kb in size. The information in the electronic format of the sequence listing is incorporated herein by reference in its entirety.

SUMMARY

In aspects, the disclosure relates to a method of identifying complexes formed by RNA molecules bound by RNA binding proteins. In some embodiments, the method includes contacting an RNA sample with one or more RNA binding proteins bound as part of a RNA-protein complex with one or more oligo conjugated entities, and ligating the RNA sample to the one or more oligo conjugated entities within each RNA-protein complex with proximity-based ligation to form one or more chimeric RNA or DNA molecules. In some embodiments, the one or more chimeric RNA or DNA molecules are amplified by PCR. In some embodiments, the one or more chimeric RNA or DNA molecules or the product from PCR amplification are sequenced. In some embodiments, the one or more oligos conjugated entities contain specific sequences capable of identifying the original complex. In some embodiments, the one or more oligos conjugated entities contain ten or less different sequences. In some embodiments, the one or more oligos conjugated entities contain ten or more different sequences. In some embodiments, the one or more oligos conjugated entities contains a randomized sequence capable of determining if a molecule is unique or a PCR duplicate. In some embodiments, the RNA sample is from mammal cells. In some embodiments, the method further includes isolating the RNA-protein complex. In some embodiments, the method further includes lysing cells prior to isolating the RNA-protein complex. In some embodiments, isolating the RNA-protein complex is by immunoprecipitation of the complex. In some embodiments, the one or more oligo conjugated entities is an antibody. In some embodiments, the one or more oligo conjugated entities is a recombinant Fab, nanobody, or aptamer. In some embodiments, the one or more oligo conjugated entities is a bead. In some embodiments, the bead is a magnetic bead capable of binding IgG antibodies. In some embodiments, the one or more oligo conjugated entities is an antibody-coupled magnetic bead. In some embodiments, the method further includes generating one or more oligo conjugated antibodies. In some embodiments, contacting the RNA sample further comprises cross-linking the RNA-protein complex together by UV light or a chemical crosslink agent. In some embodiments, the chemical crosslink agent is selected from formaldehyde, formalin, acetaldehyde, prionaldehyde, water-soluble carbomiidides, phenylglyoxal, and UDP-dialdehyde. In some embodiments, the RNA sample comprises mRNA molecules. In some embodiments, the one or more chimeric DNA molecules are formed by reverse transcribing RNA molecules into the DNA molecules before the enriching step. In some embodiments, the one or more chimeric RNA or DNA is capable of being enriched. In some embodiments, the one or more chimeric RNA or DNA is specifically amplified by PCR. In some embodiments, the specific RNA binding protein is selected from RBFOX2, PUM2, DDX2, FAM120A, ZC3H11A, SF3B4, EIF3G, LIN28B, PRPF8, IG2BP2, YTHDF2, and U2AF2. In some embodiments, the oligo is conjugated to the entity using an amine or thiol reactive probe. In some embodiments, the amine or thiol reactive probes enable oligonucleotide conjugation via click chemistry. In some embodiments, the click chemistry reaction is copper catalyzed alkyne azide cycloaddition, strained promoted alkyne azide cycloaddition, or inverse electron demand diels alder. In some embodiments, isolating the complex removes unreacted probes. In some embodiments, the method further includes amplifying the one or more chimeric RNA or DNA molecules. In some embodiments, the product of the amplified one or more chimeric RNA or DNA molecules is sequenced. In some embodiments, the method further includes identifying a computationally chimeric RNA or DNA molecule of interest.

In some embodiments, the method comprises generating an oligo conjugated antibody, contacting an RNA sample with a RBP to form a complex, isolating the RBP-RNA complex using the labeled antibody, ligating the RBP bound RNA molecule to the oligo present on the antibody to form chimeric RNA molecules, amplifying enriched chimeric RNA molecules, or cDNA molecules thereof, by PCR, sequencing the PCR products, and identifying computationally chimeric RNA molecules. In some embodiments, the method may be used to determine RNA binding proteins to specific RNA targets. In some embodiments, the sequence of the oligo is conjugated to each antibody and its chimeric RNA molecule.

In some embodiments, the generating an oligo conjugated antibody, providing RBPs and fixing or crosslinking RNAs inside the RBP to form RBP-RNA complexes, isolating RBP-RNA complexes using the labeled antibody, ligating the RBP bound RNA molecule to the oligo present on the antibody to form chimeric RNA molecules, amplifying enriched chimeric RNA molecules, or cDNA molecules thereof, by PCR, sequencing the PCR products, and identifying computationally chimeric RNA molecules. In some embodiments, the method may be used to determine RNA binding proteins to specific RNA targets. In some embodiments, the sequence of the oligo is conjugated to each antibody.

In some embodiments, the method comprises generating an oligo conjugated antibody, providing RNA, incubating the RNA with the labeled antibody targeting the modification of interest, ligating the RNA molecule to the oligo present on the antibody to form chimeric RNA molecules, amplifying enriched chimeric RNA molecules, or cDNA molecules thereof, by PCR, sequencing the PCR products, and identifying computationally chimeric RNA molecules. In some embodiments, the method may be used to determine RNA binding proteins to specific RNA targets. In some embodiments, the sequence of the oligo is conjugated to each antibody.

In some embodiments, a kit is provided. In some embodiments, a kit includes one or more oligonucleotides entities, and a manual providing instructions for identifying RNA targets of RNA binding proteins. In some embodiments, the kit further includes one or more buffers. In some embodiments, the one or more buffers is selected from the group consisting of bead elution buffer, library elution buffer, PNK buffer, RT buffer, proteinase K buffer, bead binding buffer, RNA ligation buffer, no salt buffer, lysis buffer, ssDNA ligation buffer, and high slat buffer. In some embodiments, the kit further includes one or more primers. In some embodiments, the one or more primers is selected from the group consisting of qPCR primer and ABC RT Primer.

These and other features, aspects, and advantages of the present disclosures will become better understood with reference to the following description, drawings, and claims.

BRIEF DESCRIPTION OF THE DRAWINGS

FIG. 3 illustrates the top motif identified through a de novo approach from an embodiment.

FIG. 11 illustrates a table of select barcode amplification by qPCR where BC1 = IGF2BP2, BC2 = RBFOX2, BC3 = PUM2, BC4 = FAM120A, BC5 = DDX3, BC6 = ZC3H11A, BC7 = EIF3G, BC8 = PRPF8, BC9 = LIN28B, BC10 = SF3B4. Each column has the target barcode selected for amplification colored.

DETAILED DESCRIPTION

Figure 1:
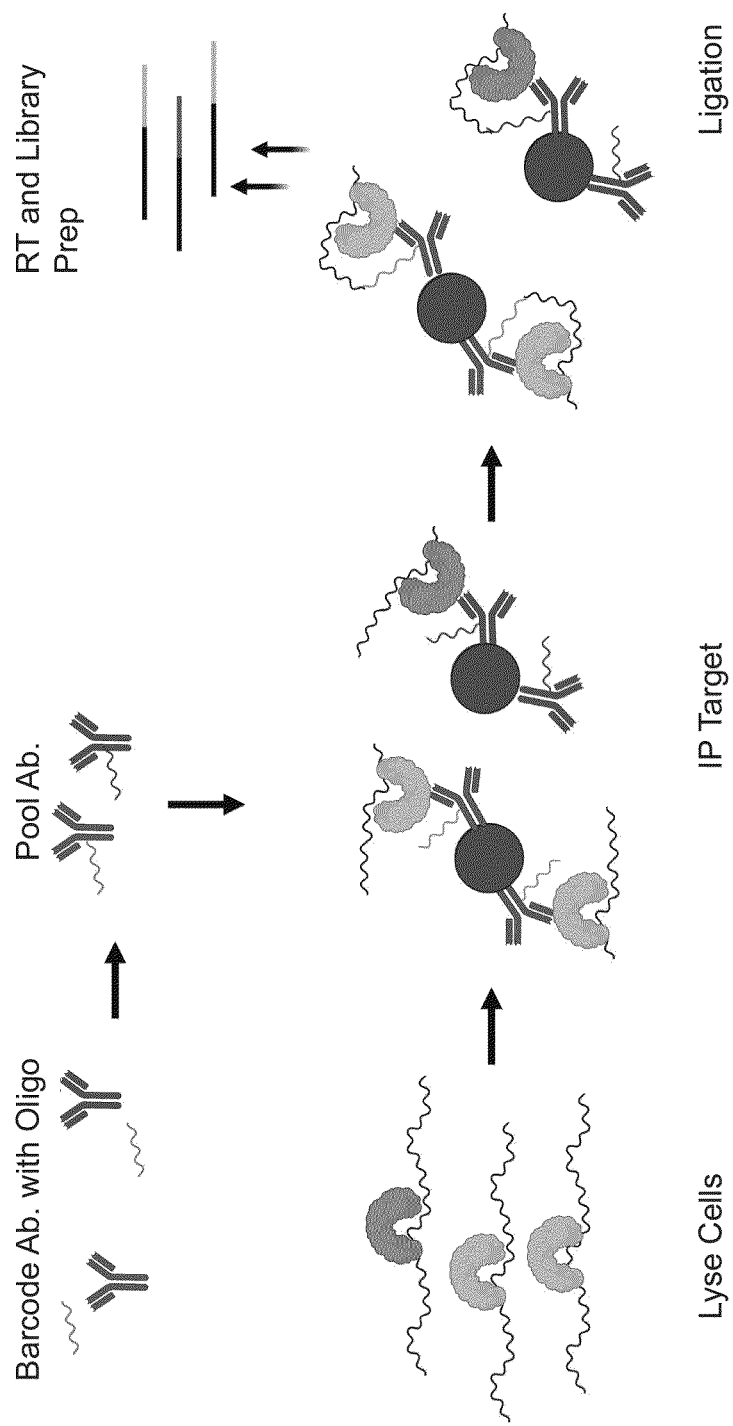
FIG. 1 illustrates a schematic diagram depicting an embodiment of a protocol for identifying RNA targest of an RBP using a oligo conjugated antibody.

In the Summary Section above and the Detailed Description Section, and the claims below, reference is made to particular features of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there is a plurality of definitions for a term herein, those in this section prevail unless stated otherwise.

As used herein, the term "eCLIP" broadly describes an enhanced version of the crosslinking and immunoprecipitation (CLIP) assay, and is used to identify the binding sites of RNA binding proteins (RBPs).

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviations, per the practice in the art. Alternatively, "about" can mean a range of up to 20%, up to 10%, up to 5%, and up to 1% of a given value. Alternatively, particularly with respect to biological systems or processes, the term can mean within an order of magnitude, within 5-fold, and within 2-fold, of a value. Where particular values are described in the application and claims, unless otherwise stated the term "about" meaning within an acceptable error range for the particular value should be assumed.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps but may include additional steps. When used in the context of a compound, composition or device, the term "comprising" means that the compound, composition or device includes at least the recited features or components but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

All references cited herein, including but not limited to published and unpublished applications, patents, and literature references, are incorporated herein by reference in their entirety and are hereby made a part of this specification.

Where a range of values is provided, it is understood that the upper and lower limit, and each intervening value between the upper and lower limit of the range is encompassed within the embodiments.

Methods

Figure 13:
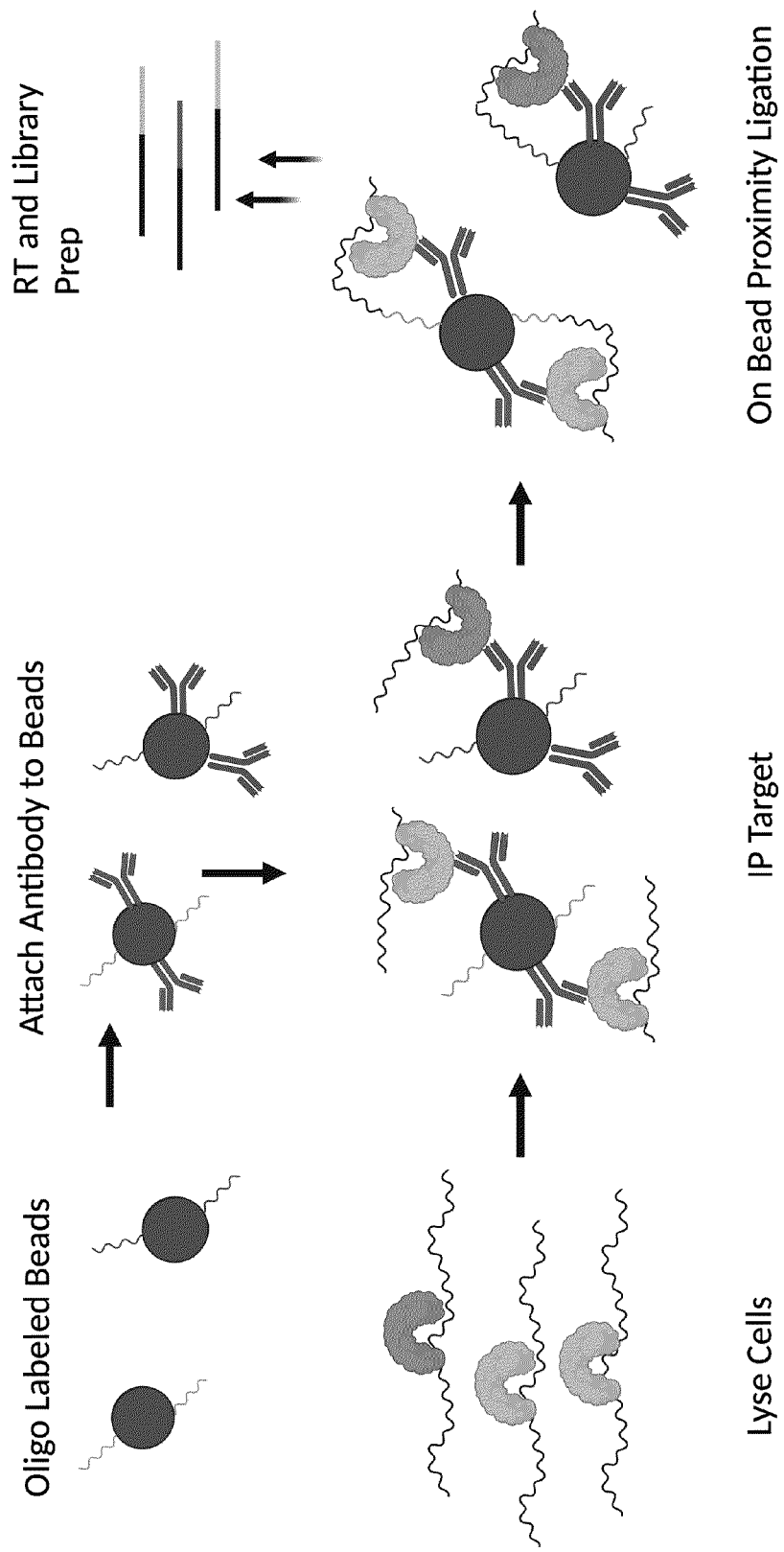
FIG. 13 illustrates a schematic diagram depicting an embodiment of a protocol for identifying RNA targets using on bead proximity ligation.

In aspects, the disclosure relates to a method of identifying RNA molecules bound by RNA binding proteins in a complex as shown in FIG. 1. In some embodiments, the method of identifying RNA targets of RNA binding proteins includes contacting an RNA sample with one or more RNA binding proteins bound as part of a RNA-protein complex with one or more oligo conjugated entities, and ligating the RNA sample to the one or more oligo conjugated entities within each RNA-protein complex with proximity-based ligation to form one or more chimeric RNA or DNA molecules. In some embodiments, the method is depicted in FIG. 13. In some embodiments, the one or more chimeric RNA or DNA molecules are amplified by PCR. In some embodiments, the one or more chimeric RNA or DNA molecules or the product from PCR amplification are sequenced. In some embodiments, the one or more oligos conjugated entities contain specific sequences capable of identifying the original complex. In some embodiments, the one or more oligos conjugated entities contain ten or less different sequences. In some embodiments, the one or more oligos conjugated entities contain ten or more different sequences. In some embodiments, the one or more oligos conjugated entities contains a randomized sequence capable of determining if a molecule is unique or a PCR duplicate. In some embodiments, the RNA sample is from mammal cells. In some embodiments, the method further includes isolating the RNA-protein complex. In some embodiments, the method further includes lysing cells prior to isolating the RNA-protein complex. In some embodiments, the one or more oligo conjugated entities is an antibody. In some embodiments, the one or more oligo conjugated entities is a recombinant Fab, nanobody, or aptamer. In some embodiments, the one or more oligo conjugated entities is a bead. In some embodiments, the specific RNA binding protein is selected from RBFOX2, PUM2, DDX2, FAM120A, ZC3H11A, SF3B4, E1F3G, Lin28B, PRPF8, and IG2BP2. In some embodiments, the chemical crosslink agent is selected from formaldehyde, formalin, acetaldehyde, prionaldehyde, water-soluble carbomiidides, phenylglyoxal, and UDP-dialdehyde. In some embodiments, the oligo is conjugated to the entity using an amine or thiol reactive probe. IN some embodiments, the amine or thiol reactive probes enable oligonucleotide conjugation via click chemistry. In some embodiments, the click chemistry reaction is copper catalyzed alkyne azide cycloaddition, strained promoted alkyne azide cycloaddition, or inverse electron demand DielsAlder reaction. In some embodiments, the isolating the complex removes unreacted probes. In some embodiments, the one or more oligo conjugated entities is an antibody-coupled magnetic bead. In some embodiments, the conjugated entity is a magnetic bead that binds IgG antibodies.

In some embodiments, the method includes generating an oligo conjugated antibody, contacting an RNA sample with a RBP to form a complex, isolating the complex using a labeled antibody, ligating the RBP bound RNA molecule to an oligo present on the antibody to form chimeric RNA molecules, amplifying enriched chimeric RNA molecules, or cDNA molecules thereof, by PCR, sequencing the PCR products, and identifying computationally chimeric RNA molecules.

In some embodiments, the method comprises generating an antibody that is conjugated to an oligonucleotide barcode. The oligonucleotide barcode may have a unique nucleotide sequence which can be used to distinguish one antibody from another antibody in a multiplexed mixture. In some embodiments, the method further comprises contacting an RNA sample with an RNA binding protein (RBP) to form a complex. In some embodiments, the RBP may be selected from, but is not limited to, RBFOX2, PUM2, DDX3, FAM120A, ZC3H11A, SF3B4, E1F3G, LIN28B, PRPF8, IG2BP2, YTHDF2, and U2AF2 proteins. In some embodiments, the method further comprises isolating the complex. In some embodiments, the method further comprises isolating the RNA binding protein-RNA complex using a barcode labeled antibody. In some embodiments, the method further comprises ligating the RBP bound RNA molecule to the oligonucleotide barcode present on the antibody to form chimeric RNA molecules. This step may be carried out by various methods such as a proximity ligation reaction. In some embodiments, the method further comprises amplifying enriched chimeric RNA molecules, or cDNA molecules thereof. In some embodiments, the method further comprises sequencing the PCR products. In some embodiments, the method further comprises identifying computationally chimeric RNA molecules.

In aspects, the disclosure relates to a method of identifying RNA molecules bound by RNA binding proteins. In some embodiments, the method comprises generating an antibody conjugated to an oligonucleotide barcode. In some embodiments, the method further providing RNA binding proteins and fixing or crosslinking RNAs inside the RNA binding protein to form RNA binding proteins-RNA complexes. In some embodiments, the method further comprises isolating the RNA binding protein-RNA complex using the labeled antibody. In some embodiments, the method further comprises ligating the RNA binding protein bound RNA molecule to the oligonucleotide conjugated to the antibody to form chimeric RNA molecules. In some embodiments, the method further comprises amplifying enriched chimeric RNA molecules, or cDNA molecules thereof. In some embodiments, the method further comprises sequencing the PCR products. In some embodiments, the method further comprises identifying computationally chimeric RNA molecules. In some embodiments, the method comprises generating an oligo conjugated antibody, contacting an RNA sample with a RBP to form a complex, isolating the RBP-RNA complex using the labeled antibody, ligating the RBP bound RNA molecule to the oligo present on the antibody to form chimeric RNA molecules, amplifying enriched chimeric RNA molecules, or cDNA molecules thereof, by PCR, sequencing the PCR products, and identifying computationally chimeric RNA molecules.

In some aspects, the disclosure relates to a method of identifying sites of RNA modification. In some embodiments, the method comprises generating an antibody that is conjugated to an oligonucleotide barcode. In some embodiments, the method further comprises providing RNA and incubating the RNA with the conjugated antibody targeting the modification of interest. In some embodiments, the method comprises ligating the RNA molecule to the oligo present on the antibody to form chimeric RNA molecules. In some embodiments, the method further comprises amplifying enriched chimeric RNA molecules, or cDNA molecules thereof. In some embodiments, the method comprises sequencing the PCR products. In some embodiments, the method further comprises identifying computationally chimeric RNA molecules. In some embodiments, the method comprises generating an oligonucleotide conjugated antibody, providing RNA, incubating the RNA with the labeled antibody targeting the modification of interest, ligating the RNA molecule to the oligo present on the antibody to form chimeric RNA molecules, amplifying enriched chimeric RNA molecules, or cDNA molecules thereof, by PCR, sequencing the PCR products, and identifying computationally chimeric RNA molecules.

In some embodiments, the antibody for the RNA binding protein or RNA modification of interest may be conjugated to a DNA or RNA oligo through click chemistry. In this embodiment the antibody may be labeled with a click chemistry reactive probe and the oligo with the complementary reactive probe. The oligo and antibody are then mixed and allowed to react forming the final antibody-oligo conjugate. These click chemistry probes pairs may include, but are not limited to: Azide/Alkyne, DBCO/Azide, or Tetrazine/TCO probe pairs.

In some embodiments, the method may include combining multiple antibodies in the same sample to form a multiplexed mixture. In some embodiments, each antibody can be conjugated with an oligonucleotide containing a unique barcode sequence. Through data analysis, if the sequences of barcode are known, the RNA binding protein bound by the antibody, or modification of interest can be assigned from a mixed sample of labeled antibodies. Individual RNA molecules can then be attributed to each antibody through the chimeric read structure of the resulting chimeric RNA formed by the barcode and the RNA bound by the RBP.

In some embodiments, the target RNA sample may be taken from cells or tissue. Some embodiments further include lysing cells prior to isolating the complexes formed from the RNA and RNA binding proteins. During the lysing process, cells may be incubated with lysis buffer and sonicated. In some embodiments, the lysing process further includes using RNase, such as RNase I, to partially fragment RNA molecules.

Some embodiments of the present disclosure relate to a method that can definitively identify direct RNA-target interactions with targeted proteins without the requirement for immunoprecipitation or gel extraction.

In some embodiments, after the RNA and target RNA binding protein are bound into a complex, the RNA and protein are crosslinked together by UV light or a chemical crosslinking agent. In some embodiments, the chemical crosslinking agent may be formaldehyde. In some embodiments, the UV light or chemical crosslinking agent links the RNA and target RNA binding protein. This can preserve the RNA integrity and also the binding relationship between the RNA and its target RNA binding protein during the purification steps.

In some embodiments, isolating the RNA binding protein-RNA complex is done by immunoprecipitation of the complex. In some embodiments, the immunoprecipitation may include contacting the complex with an oligo conjugated antibody that is specific for the target RNA binding protein. In some embodiments, the immunoprecipitation may include incubating the crosslinked RNA sample or lysed cells with magnetic beads which are pre-coupled to a secondary antibody that binds with the oligo conjugated primary antibody. The beads may bind to any complexes that contain the target RNA binding protein. In some embodiments, using a magnet, the beads along with the RNA binding protein complexes can be separated from the mix.

In some embodiments, beads can be added to an embodiment of the methods described herein. In some embodiments, the beads may be approximately 1 μm in size. In some embodiments, the beads may be magnetic beads. In some embodiments, the beads may be superparamagnetic particles with a bound protein. In some embodiments, the bound protein may be selective for biotin. In some embodiments, the bound protein is Streptavidin. In some embodiments, the beads are streptavidin magnetic beads. In some embodiments, the bound protein may be selective for antibodies. In some embodiments, the bound protein may be selective for anti-IgG. In some embodiments, the beads are dynabeads. In some embodiments, the beads are anti-rabbit Dynabeads. In some embodiments, the bead is a BcMag magnetic bead. In some embodiments, the beads are mono-avidin magnetic beads. In some embodiments, an on-bead probe can be added to an embodiment described herein. In some embodiments, the on-bead probe can target and enrich libraries in chimeric reads specific to one or more RNA of interest.

In some embodiments, a method may further include an enrichment step. In some embodiments, the enrichment step increases a proportion of chimeric reads. In some embodiments, the enrichment step may produce chimeric reads out of all uniquely mapped reads of at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, or ranges including and/or spanning the aforementioned values. In some embodiments, the enrichment step may produce 5% to 30% chimeric reads out of all uniquely mapped reads.

Some embodiments further include immunoprecipitated RNA end repair. In some embodiments, after the RNA binding protein complexes are isolated, an entity conjugated oligo and its RNA binding protein target RNA molecules are ligated together to form oligo-target RNA chimeric molecules. Some embodiments further include repairing RNA ends using FastAP, a phosphatase that removes 5'-phosphate from RNA-DNA chimeric molecules, and/or T4 PNK, which converts 2'-3'-cyclic phosphate to 3'-OH that is needed for further ligation.

In some embodiments, the method may further include the addition of a unique molecular identifier (UMI). In some embodiments, the UMI may be added into the entity conjugated oligo to facilitate further processes. In some embodiments, the method may further include the addition of a randomer added into the antibody conjugated oligo to facilitate further processes. In some embodiments, the UMI may be a PCR duplicate removal. In some embodiments, the UMI may be an adapter-specific UMI. In some embodiments, the UMI may be a fragment-specific UMI. In some embodiments, the UMI may be nonrandom UMIs.

In some embodiments, the RNA may be first ligated with a reverse transcription adapter and the entity is instead conjugated with a template switch oligo allowing for incorporation of the barcode only in transcripts successfully converted to cDNA.

In some embodiments, the RNA binding protein/antibody complexes may be incubated with proteases to digest the RNA binding protein/antibody and release the ligated RNA fragments from the formed complex.

In some embodiments, the sequences of RNA molecules are known, probes can be designed to specifically bind to those RNA molecules. Such probes can specifically bind to non-chimeric RNA molecules, as well as RNA-target antibody oligo RNA chimeric molecules for enrichment. In some embodiments, the probes may be 100% complementary to the RNA molecules and in some cases the probes can include additional sequences to better cover imprecisely processed RNAs. In some embodiments, the mixture of RNA molecules is reverse transcribed into cDNA molecules before adding probes. In some embodiments, the probes are anti-sense nucleic acid probes having a length between 10 bp and 5 kb. In some embodiments, the probes are anti-sense nucleic acid probes in a length of 10 bp, 20 bp, 30 bp, 40 bp, 50 bp, 60 bp, 70 bp, 80 bp, 90 bp, 100 bp, 150 bp, 200 bp, 250 bp, 300 bp, 350 bp, 400 bp, 450 bp, 500 bp, 550 bp, 600 bp, 650 bp, 700 bp, 750 bp, 800 bp, 850 bp, 900 bp, 1000 bp, 1100 bp, 1200 bp, 1300 bp 1400 bp, 1500 bp, 1600 bp, 1700 bp, 1800 bp, 1900 bp, 2000 bp, 2100 bp, 2200 bp, 2300 bp, 2400 bp, 2500 bp, 2600 bp, 2700 bp, 2800 bp, 2900 bp, 3000 bp, 3100 bp, 3200 bp, 3300 bp, 3400 bp, 3500 bp, 3600 bp, 3700 bp, 3800 bp, 3900 bp, 4000 bp, 4100 bp, 4200 bp, 4300 bp, 4400 bp, 4500 bp, 4600 bp, 4700 bp, 4800 bp, 4900 bp, 5000 bp, or ranges including and/or spanning the aforementioned values. In some embodiments, the probes may be between 10 bp and 1 kb, 10 bp and 500 bp, 10 bp and 250 bp, 10 bp and 100 bp, or 10 bp and 50 bp in length.

In some embodiments, the probes may be RNA, single stranded DNA (ssDNA), or synthetic nucleic acids, such as a locked nucleic acid (LNA). A LNA is often referred to as inaccessible RNA and is a modified RNA nucleotide in which the ribose moiety is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired and hybridize with DNA or RNA according to Watson-Crick base-pairing rules. The locked ribose conformation enhances base stacking and backbone pre-organization. In some embodiments, this may significantly increase the hybridization properties (melting temperature) of oligonucleotides.

In embodiments that are focused on genes or sites of interest, targeted PCR may be performed to rapidly analyzed binding at the target location without the need for sequencing.

In embodiments that include crosslinking, the binding relation between the RNA and its target RBP or antibody are preserved. Thus, a method according to some embodiments can definitively identify direct RBP-RNA interactions.

In some embodiments, the RNA sample includes messenger RNA (mRNA) molecules.

In some embodiments, the methods described herein can omit a gel clean up step. In some embodiments, omitting the gel clean up step may create a simplified high throughput version of the method.

Kits

Embodiments also include kits containing the components required to perform the methods and assays described herein. For example, the kit may contain unconjugated oligos, ligase, RNA binding proteins, anti-RNA binding protein antibodies, conjugation reagents. In some embodiments, the kit may include one or more beads. The beads may be labeled with oligonucleotides. The beads may be specific for anti-IgG. The beads may be magnetic. In some embodiments, the kit may include one or more buffers and reagents. In some embodiments, the kit may include a ssDNA adapter. The ssDNA adapter may include ABCi7primer, DMSO, and bead elution buffer. In some embodiments, the kit may include a RT adapter. In some embodiments, the kit may include one or more RT primers. The RT adapter may include dNTPs and an ABC RT primer. In some embodiments, the kit may include a bead elution buffer. The bead elution buffer may include TWEEN® 20, Tris buffer, and EDTA. In some embodiments, the kit may include a library elution buffer. The library elution buffer may include Tris buffer, EDTA and sodium chloride. In some embodiments, the kit may include qPCR primers. In some embodiments, the kit may include PNK buffer. The PNK buffer may include Tris buffer, magnesium chloride, and ATP. In some embodiments, the kit may include a RT buffer. In some embodiments, the RT buffer includes SuperScript III RT buffer and DTT. In some embodiments, the kit may include a proteinase K buffer. The proteinase K buffer may include Tris buffer, sodium chloride, EDTA, and SDS. In some embodiments, the kit may include bead binding buffer. The bead binding buffer may include a RLT buffer and TWEEN® 20. In some embodiments, the kit may include a RNA ligation buffer. The RNA ligation buffer may include Tris buffer, magnesium chloride, DMSO, Tween 20, ATP, and PEG. In some embodiments, the kit may include a no salt buffer. The no salt buffer may include Tris buffer, magnesium chloride, Tween 20, and sodium chloride. In some embodiments, the kit may include lysis buffer. The lysis buffer may include Tris buffer, sodium chloride, IGEPAL, SDS, and sodium deoxycholate. In some embodiments, the kit may include ssDNA ligation buffer. The ssDNA ligation buffer may include Tris buffer, magnesium chloride, DMSO, DTT, Tween 20, ATP and PEG8000. In some embodiments, the kit may include a high salt buffer. The high salt buffer may include Tris buffer, sodium chloride, EDTA, IGEPAL, SDS, and sodium deoxycholate. In some embodiments, the kit may include a mRNA Elution buffer. The mRNA Elution buffer may include Tris buffer and EDTA.

The components of the kit may be combined in one container, or each component may be in its own container. For example, the components of the kit may be combined in a single reaction tube or in one or more different reaction tubes. Further details of the components of this kit are described above. The kit may also contain other reagents described above and below that are not essential to the method but nevertheless may be employed in the method, depending on how the method is going to be implemented.

EXAMPLES

Examples are provided herein below. However, the presently disclosed and claimed inventive concepts are to be understood to not be limited in their application to the specific experimentation, results and laboratory procedures. Rather, the Examples are simply provided as one of various embodiments and are meant to be exemplary, not exhaustive.

Example 1

In this example, an embodiment of a method for identifying RNA targets of an RNA binding protein of interest from cells or tissues is described.

First, an oligonucleotide containing a UMI and/or a barcode was conjugated to an antibody targeting a RBP of interest (RBFOX2). The antibody was labeled with an amine reactive probe containing a DBCO (diarylcyclooctyne) click chemistry handle. Next, the antibody was purified to remove any unreacted probe. A custom 3' amine RNA oligonucleotide barcode and a 3' amine DNA oligonucleotide barcode were used as the amine reactive probes to attach to the complementary click chemistry azide probe. Next, the oligo was purified to remove unreacted probe. Each of the oligos were attached to the RBFOX2 antibody through click chemistry by mixing the two components (antibody and either oligo barcode) together.

Figure 4:
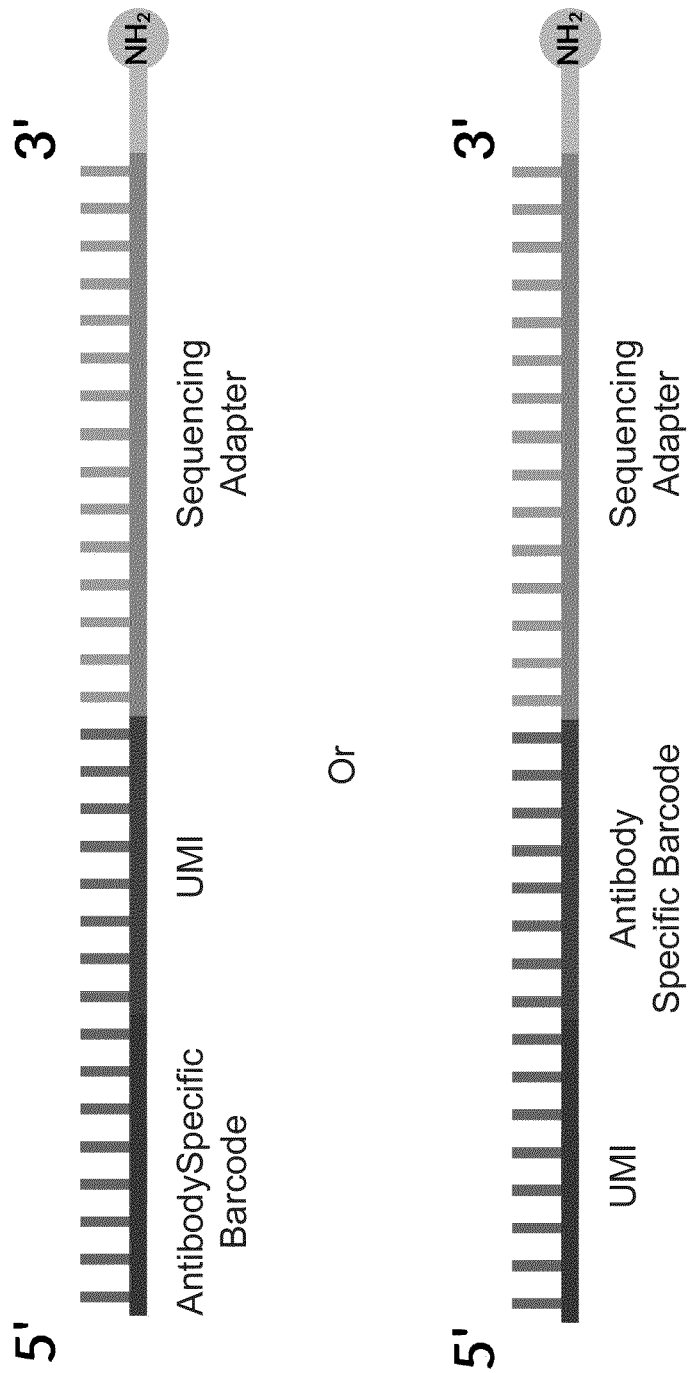
FIG. 4 illustrates a schematic depicting an embodiment of an oligo used for conjugation to the antibody.

Second, the crosslink cells or tissues with the RNA binding proteins were linked to their bound RNA molecules by a process shown in FIG. 4.

Third, the lysed cells (lysis buffer and sonication) and/or RNase treated lysate (RNase 1) were applied to the partially fragment RNA, and coupled to beads which were pre-coupled to the RBFOX2 oligo conjugated antibody from step 1 (Immunoprecipitation of RBFOX2 protein).

Fourth, wash the previous step to remove the background.

Fifth, the 3' RNA ends were repaired using T4 PNK, leaving 3'-OH that was needed for ligation.

Figure 5:
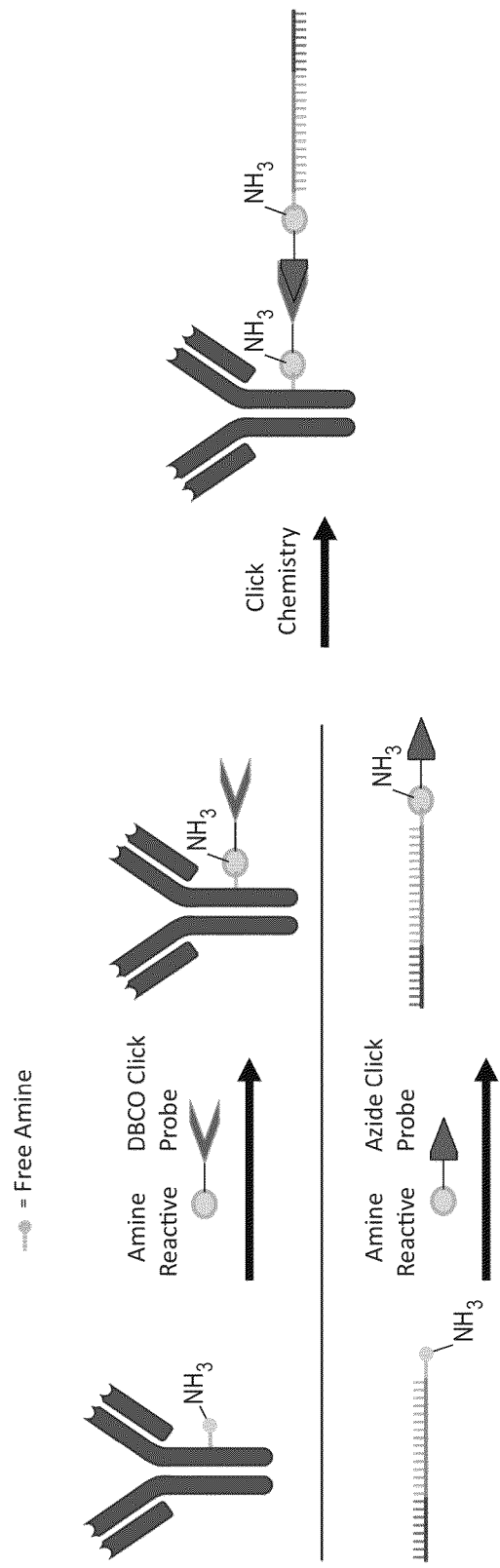
FIG. 5 illustrates a schematic depicting an embodiment of a click chemistry reaction to conjugate an oligo to an antibody.

Sixth, a proximity based intermolecular ligation was performed using ligase to form chimeric RNA to antibody oligo molecules as shown in FIG. 5.

Seventh, strong washes were performed to remove background.

Eighth, the RNA binding protein and antibody peptides are digest using protease K releasing the oligo-RNA chimera.

Ninth, the RNA molecules were reverse transcribed to convert into cDNA.

Tenth, the cDNA was cleaned up to prepare for step 12.

Eleventh, the second adapter ligation was performed with UMI.

Twelfth, the libraries were PCR amplified and cleaned up for sequencing.

Thirteenth, the libraries made of the PCR produces was sequenced.

Figure 2:
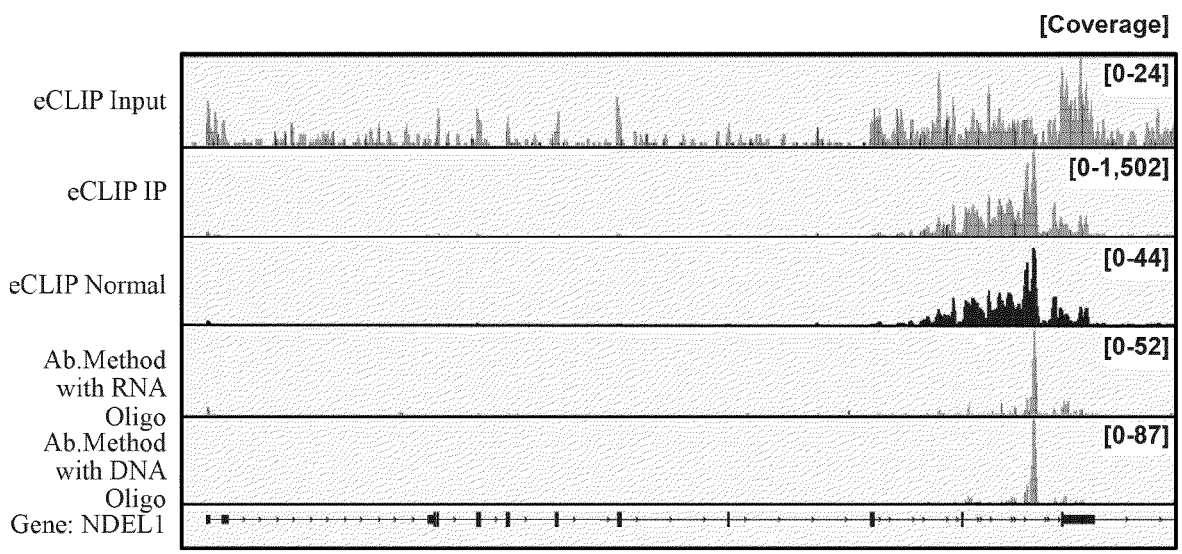
FIG. 2 illustrates a genome track view of one binding site identified in comparison eCLIP.

Fourteenth, the data was analyzed as shown in FIG. 2. As shown the antibody methods with either the RNA oligonucleotide barcode or the DNA oligonucleotide barcode were very specific for detecting the same peaks of RNA binding as prior eCLIP processes, indicating that the method worked to detect RNA molecules bound to the target RBP complexes.

Further, the example above may include trimming N10 UMIs from the 5' ends of R1 reads and save the UMI sequences in the read names to be utilized in subsequent steps, trimming 3' sequencing adapters, mapping reads to a reference genome, removing PCR duplicates by utilizing UMI sequences from the read names and mapping positions, Calling peaks from aligned reads, filtering peaks for high confidence sites and assign as binding targets of RNA binding proteins, and performing de novo motif discovery to identify possible binding motifs.

If the purpose of the experiment is designed to identify RNA targets for a known RNA binding protein or set of RNA binding proteins, such RNA targets will be identified following the steps described herein.

Example 2

This example is a protocol for a 10-plex experiment according to an embodiment of the disclosure.

Buffer Compositions and Reagents ssDNA Adapter: 50 µl 100 µM ABCi7primer, 60 µl DMSO, 140 µL Bead Elution Buffer Bead Elution Buffer: 0.001% TWEEN® 20, 10 mM Tris pH 7.5, 0.1 mM EDTA Library Elution Buffer: 20 mM Tris pH 7.5, 0.2 mM EDTA, 5 mM NaCl qPCR Primers: 1.25 mM Primer 1, 1.25 mM Primer 2

RT Primer: 6.7 mM each dNTP, 3.3 µM ABC RT Primer

PNK Buffer: 97.2 mM Tris pH 7, 13.9 mM $MgCl_2$, 1 mM ATP

RT Buffer: 2.17x SUPERSCRIPT™ III RT buffer, 10 mM DTT

Proteinase K Buffer: 100 mM Tris pH 7.5, 50 mM NaCl, 10 mM EDTA, 0.2% SDS

Bead Binding Buffer: 1X RLT buffer, 0.01% TWEEN® 20

RNA Ligation Buffer: 75 mM Tris pH 7.5, 16.7 mM MgCl$_2$, 5% DMSO, 0.00067% TWEEN® 20, 1.67 mM ATP, 25.7% PEG8000

25X No Salt Buffer: 500 mM Tris pH 7.4, 250 mM MgCl$_2$, 5% TWEEN® 20, 125 mM NaCl Lysis Buffer: 50 mM Tris pH 7.4, 100 mM NaCl, 1% IGEPAL, 0.1% SDS, 0.5% Sodium Deoxycholate ssDNA Ligation Buffer: 76.9 mM Tris pH 7.5, 15.4 mM MgCl$_2$, 3% DMSO, 30.8 mM DTT, 0.06% TWEEN® 20, 1.5 mM ATP, 27.7% PEG8000

High Salt Buffer: 50 mM Tris pH 7.4, 1 M NaCl, 500 mM EDTA, 0.5% IGEPAL, 1% SDS, 0.5% sodium deoxycholate

TABLE 1

Barcode Sequence

| RBP | Barcode Sequence | SEQ ID NO |
|---|---|---|
| RBFOX2 | /5Phos/ATTACTCGNNNNNNNNAGATCGGAAGAGCGTCGTGT/3AmMO/ | 1 |
| PUM2 | /5Phos/TCCGGAGANNNNNNNNAGATCGGAAGAGCGTCGTGT/3AmMO/ | 2 |
| DDX3 | /5Phos/CGCTCATTNNNNNNNNAGATCGGAAGAGCGTCGTGT/3AmMO/ | 3 |
| FAM120A | /5Phos/GAGATTCCNNNNNNNNAGATCGGAAGAGCGTCGTGT/3AmMO/ | 4 |
| ZC3H11A | /5Phos/ATTCAGAANNNNNNNNAGATCGGAAGAGCGTCGTGT/3AmMO/ | 5 |
| SF3B4 | /5Phos/GATTCGTNNNNNNNNAGATCGGAAGAGCGTCGTGT/3AmMO/ | 6 |
| EIF3G | /5Phos/CTGAAGCTNNNNNNNNAGATCGGAAGAGCGTCGTGT/3AmMO/ | 7 |
| LIN28-B | /5Phos/TAATGCGCNNNNNNNNAGATCGGAAGAGCGTCGTGT/3AmMO/ | 8 |
| PRPF8 | /5Phos/CGGCTATGNNNNNNNNAGATCGGAAGAGCGTCGTGT/3AmMO/ | 9 |
| IG2BP2 | /5Phos/TCCGCGAANNNNNNNNAGATCGGAAGAGCGTCGTGT/3AmMO/ | 10 |

TABLE 2

Sequence

| Oligo | Sequence | SEQ ID NO |
|---|---|---|
| ABC RT Primer | ACACGACGCTCTTCC | 11 |
| ABC i7 Primer | /5Phos/AGATCGGAAGAGCACACGTCTG/3SpC3 | 12 |
| Index Primer 501 | AATGATACGGCGACCACCGAGATCTACACTATAGCCTACACTCTTTCCCTACACGACGCTCTTCCGATCT | 13 |
| Index Primer 701 | CAAGCAGAAGACGGCATACGAGATCGAGTAATGTGACTGGAGTTCAGACGTGTGCTCTTCCGATCT | 14 |

TABLE 3

Sequence

| qPCR Primer | Sequence | SEQ ID NO |
|---|---|---|
| Primer1 | ACACGACGCTCTTCC | 15 |
| Primer2 | /5Phos/AGATCGGAAGAGCACACGTCTG/3SpC3 | 16 |

TABLE 4

Reagents

| Vendor | Part # | Reagent |
|---|---|---|
| New England Biolabs® | M0331B | 5′ Deadenylase |
| New England Biolabs® | M0544B | NEB NEXT® Ultra™ II Q5® Master Mix |
| New England Biolabs® | P8107B | Proteinase K, Molecular Biology Grade |
| New England Biolabs® | M0314B | RNase Inhibitor, Murine |
| New England Biolabs® | M0201B | T4PNK |
| New England Biolabs® | M0437B-BM | T4 RNA Ligase 1 (ssRNA Ligase) |
| ThermoFisher | EP1756-B012 | SuperScript™ III Reverse Transcriptase Suppled with: 5X First-Strand Buffer - 1× 20 ml. Concentration 200 U/μl Pack Size 200 KU |
| ThermoFisher | 11204D | Dynabeads™ M-280 Sheep-A-RABBIT-10 ml |
| ThermoFisher | AM2239-B001 | TURBO™ DNase Supplied with: 10X TURBO™ DNase Buffer – 7x 1.85 ml |
| ThermoFisher | EF0652-B001 | FastAP Thermosensitive AP Supplied with: 10X Buffer for fastAP – 10X 1.5 ml |
| Click Chemistry Tools | A124-10 | DBCO-PEG4-NHS Ester (10 mg) |
| Click Chemistry Tools | 1251-5 | 6-Azidohexanoic Acid Sulfo-NHS Ester (5 mg) |
| ThermoFisher | 89882 | Zebra™ Spin Desalting Columns, 7 K MWCO, 0.5 ml |
| Corning | 21-040-CV | PBS |
| ThermoFisher | AM2295 | RNase 1 |
| ThermoFisher | 87786 | Halt™ Protease Inhibitor Cocktail (100x) |
| ThermoFisher | 75001.10.ml | ExoSAP-IT™ Express PCR Product Cleanup Reagent |
| Bethyl | A301-524A | ZC3H11A |
| Bethyl | A300-864A | RBFOX2 |
| Bethyl | A300-202A | PUM2 |
| MBL | RN008p | IGF2BP2 |
| Bethyl | A303-950A | SF3B4 |
| Bethyl | A303-921A | PRPF8 |
| Aviva | AR-P67917-P050 | YTHDF2 |
| Bethyl | A303-666A | U2AF2 |
| Bethyl | A303-889 | FAM120A |
| Bethyl | A303-588A | LIN28B |
| Bethyl | A301-755A | EIF3G |
| Bethyl | A300-474A | DDX3 |

Prepare Cell Pellets UV Crosslinking of Adherent Cells

For this example, the equipment and materials included the following: UV Crosslinker with 254 nm wavelength UV bulbs, 1x PBS, Standard cell counting system, Liquid nitrogen, and Trypan blue stain.

Cell Viability Validation Prior TO Crosslinking

First, Trypan blue stain (Thermo Fisher Scientific, cat. #15250061) or an equivalent live cell counting assay was used to valuate cell viability. Next, cell viability was reviewed to confirm it was > 95% to ensure intact RNA. Cells were grown to a proper confluence, in most cases the cells were grown to 75% confluence.

Wash Cells

First, the spent media was aspirated. Second, wash the plate gently with PBS at room temperature (15 mL for a 15 cm plate). Third, carefully aspirate PBS. Fourth, add enough PBS to just cover the plate (5 mL for a 15 cm plate).

UV Crosslinking

First, the tissue culture plate was placed on leveled ice or on a cooling block pre-chilled to 4° C. Second, the above (plate plus ice or cooling block) was placed into the UV cross-linker. Third, the tissue culture plate lid for cross-linking was removed. Fourth, crosslink at 254-nm UV with an energy setting of 400 mJoules/cm$^2$. Fifth, while keeping the cells on ice, a cell scraper (Corning, cat. #CLS3010-10EA) was used to scrape the plate. Sixth, the cells were transferred to a 50 mL conical tube. Seventh, the plate was washed once with 10 mL of 1 PBS and added to the same 50 mL tube. Eight, gently resuspended until the sample was homogeneous. Ninth, the cell concentration was counted(either with automated cell counter or hemocytometer). Tenth, the 50 mL conical tube was centrifuged at 200 × g for 5 minutes at room temperature. Eleventh, the sample was aspirated and discarded supernatant. Twelfth, the desired amount of PBS for flash freezing was resuspended (typically 10×10$^6$ cells per mL). Thirteenth, the sample was transferred with a desired amount into 1.5 mL Eppendorf Safe-Lock Tubes (typically 1 mL of 10×10$^6$ cells per mL). Fourteenth, the sample was spun down at 200 × g for 5 minutes at room temperature. Fifteenth, the supernatant was aspirated and the cell pellets were frozen quickly by submerging the 1.5 mL Eppendorf tubes completely in liquid nitrogen. Sixteenth, after frozen (at least thirty seconds), the sample was removed from the liquid nitrogen and store at -80° C.

Prepare Antibody Conjugates

First, buffer exchanged zeba column 3X with 300 µl PBS at 1,500 XG for 1 min. Marked column orientation. Second, diluted 20 µg antibody in PBS up to 70 µl (-1.33E-10 mol). Third, added antibody to zeba column, centrifuge 1,500 XG for 1 min, and saved flow through in a new epitube (~70 µl). Fourth, added 0.33 µl DBCO-NHS and rotated at RT for 1 hour (25× equiv). Fifth, buffered exchange zeba column 3X with 300 µl PBS at 1,500 XG for 1 min. Marked column orientation. Sixth, added antibody reaction to zeba column, centrifuge 1,500 XG for 1 min, and saved flowthrough in a new epitube (~70 µl).

Prepare Oligo for Conjugation

First, 100 µl 100 µM Oligo in PBS with 10 uL 10 mM Azide-NHS (10× equivalent) was mixed. The sequences for all 10 oligos are listed in Table 1. Second, rotated at RT for 2 hours. Third, the exchange zeba column 3X with 300 µl PBS was buffered at 1,500 XG for 1 min. Marked column orientation. Fourth, oligo reaction was added to zeba column, centrifuge 1,500 XG for 1 min, and saved flowthrough in a new epitube (~110 µl).

Conjugate Antibody and Oligo

First, total antibody reaction mixture (~75 µl) was mixed with 6.65 µL Oligo reaction mixture (5x equiv). Second, rotated overnight at RT. Third, used directly for IP as antibody (assume 100% yield with 20 µg).

Library Prep

Preparation

First, set chiller on sonicator to 4° C. Second, prewarmed Thermomixer to 37° C. Third, set chiller on centrifuge to 4° C.

Procedure

Cell/Tissue Lysis

First, the lysis mix was prepared for each crosslinked cell pellet according to Table 5.

TABLE 5

| Lysis mix (per one pellet of 10 million cells) | |
|---|---|
| Reagent | Volume (µL) |
| Lysis Buffer | 1000 |
| Protease Inhibitor Cocktail | 5 |
| RNase Inhibitor | 10 |
| Total: | 1015 |

Second, the tubes were retrieved containing pellets from -80° C. and quickly 1 mL of cold lysis mix (do not thaw pellets on ice first) was added. Third, the pellets were gently mixed until sample was fully resuspended. Fourth, cell tubes were placed on ice for 5 minutes. During lysis, periodically pipette mixed tubes slowly. Fifth, transported samples to sonicator. If necessary, transfer to appropriate pre-chilled tubes for sonication equipment. Sixth, sonicated at 4° C. to disrupt chromatin and fragment DNA (see Table 6 below for settings).

TABLE 6

| Sonicator reference settings | | | |
|---|---|---|---|
| Sonicator | Energy setting | Set time | Cycles |
| QSonica Q800R | 75% amplitude | 5 minutes (total time is 10 min) | 30 seconds ON / 30 seconds OFF |

First, RNase-I 25-fold in 1× PBS was diluted. Second, 5 µL of Turbo DNase to each sample on ice was added to the lysed cells. Third, 10 µL of diluted RNase-I to each sample on ice was added. Proceeded immediately to next step. Fourth, incubated in thermomixer at 37° C. for 5 minutes with interval mixing at 1,200 rpm to fragment RNA. Fifth, immediately following incubation, moved all samples to ice for 3 minutes. Sixth, centrifuged samples at 12,000 × g for 3 minutes at 4° C. to pellet cellular debris. Seventh, transferred supernatant (clarified lysate) to fresh labeled 1.5 mL LoBind tubes without disturbing cell pellet. Eighth, left clarified supernatant on ice until Immunoprecipitation as described herein. Ninth, discarded cell pellets.

Preparation

First, the Lysis Buffer was inverted to mix before use. Second, the High-Salt Buffer (HSB) and 25× NoS (No-Salt) Buffer Concentrate was placed at 4° C. overnight to thaw.

Procedure

Coupling primary antibody to magnetic beads pre-coupled with secondary antibody (Repeat for EACH antibody separately). First, magnetic Dynabeads anti-Rabbit were mixed until homogeneous. Second, transferred 25 µL Dynabeads anti-Rabbit per sample into a fresh 1.5 mL LoBind tube (e.g. for 3 samples use 75 µL of secondary beads). Third, 200 µL of Lysis Buffer (chilled) was added to the tube with secondary beads. Fourth, placed the tube on DynaMag-2 magnet. Fifth, after separation was complete and supernatant was transparent (~ 1 minute), carefully aspirated and discarded the supernatant without disturbing beads. Sixth, the tube from the magnet was removed. Seventh, 500 µL Lysis Buffer (chilled) to the tube was added, closed the tube and inverted mix until homogeneous. Eighth, placed the tube on DynaMag-2 magnet. Ninth, after separation was complete and supernatant was transparent (~ 1 minute), carefully aspirated and discarded supernatant without disturbing beads. Tenth, the tube from the magnet was removed. Eleventh, repeated steps 7-10 once for a total of two washes. Twelfth, 50 µL Lysis Buffer (chilled) per sample was added to the tube. Thirteenth, 5 µg of primary antibody per sample was added to the tube containing washed beads. Fourteenth, placed tube on tube rotator and allowed beads and antibody to couple for 1 hour at room temperature.

Immunoprecipitation (IP)

First, the antibody-coupled magnetic bead tubes was removed from rotator. Second, to each antibody-coupled magnetic bead tube, 500 µL Lysis Buffer (chilled) was added. Third, inverted mix until homogenous. Fourth, placed tubes on DynaMag-2 magnet to separate beads and allowed at least 1 minute for bead separation. Fifth, when separation was complete and liquid was transparent, carefully aspirated and discarded supernatant without disturbing beads. Sixth, repeated steps 2-5 for a total of 2 washes. Seventh, removed tubes from magnet. Eighth, added 50 µL Lysis Buffer (chilled) per sample to the tubes. Ninth, added 50 uL of EACH antibody coated bead to the 1 mL of clarified lysate containing fragmented RNA and slowly pipetted to mix until homogeneous. This should total 500 uL of beads when using 10 RBP targets. Tenth, rotated immunoprecipitation tubes containing fragmented RNA and antibody-coupled magnetic beads overnight at 4° C.

Stopping Point: Samples rotate overnight at 4° C. for up to 16 hours

Preparation

First, diluted 25× NoS (No-Salt) Buffer Concentrate to 1× by adding 2 mL of concentrate to 48 mL of water. Second, prewarmed Thermomixer to 37° C. Third, prepared HSB+ (see Table 7).

TABLE 7

| Preparation of HSB+ (per sample) | |
| --- | --- |
| Component | Volume (µL) |
| 8 M LiCl | 50 |
| High-Salt Buffer (HSB) | 450 |
| Total: | 500 |

Procedure

First Immunoprecipitation (IP) Wash

First, placed IP tubes on DynaMag-2 magnet to separate beads. Second, allowed at least 1 minute for bead separation. Third, when separation was complete and liquid was transparent, carefully aspirated and discarded supernatant without disturbing beads. Forth, removed IP tubes from magnet. Fifth, added 500 µL cold HSB. Sixth, inverted mix until homogeneous. Seventh, placed on DynaMag-2 magnet. Eighth, while on magnet, slowly inverted closed tubes as beads start to separate to capture any beads from cap. Ninth, when separation was complete, and liquid was transparent, gently opened tubes and discard supernatant without disturbing beads. Tenth, removed IP tubes from magnet and added 500 µL cold HSB+ (see Table 7). Eleventh, closed tubes well and vortexed for 15 seconds. Twelfth, incubated on tube rotator for 3 min at room temperature. Thirteenth, placed on DynaMag-2 magnet. Fourteenth, while on magnet, slowly inverted closed tubes as beads start to separate to capture any beads from cap. Fifteenth, when separation was complete, and liquid was transparent, gently opened tubes and discarded supernatant without disturbing beads.

Sixteenth, repeated steps 5-9 for an additional round of HSB wash. Seventeenth, removed IP tubes from magnet. Eighteenth, added 500 µL cold 1× NoS Buffer. Nineteenth, inverted mix until homogenous. Twentieth, placed on DynaMag-2 magnet. Twenty-first, while on magnet, slowly inverted closed tubes as beads start to separate to capture any beads from cap. Twenty-two, removed IP tubes from magnet. Twenty-third, added 500 µL cold 1× NoS Buffer. Twenty-four, inverted mix until homogeneous. Twenty-five, separated beads on magnet and removed supernatant without disturbing beads. Twenty-six, spin all samples in mini-centrifuge for 3 seconds. Twenty-seven, placed samples back on magnet and allow 1 minute for bead separation. Twenty-eight, pipetted and discarded any excess liquid without disturbing beads. Twenty-nine, removed IP tubes from magnet. Thirtieth, added 500 µL cold 1× NoS Buffer. Thirty-one, inverted to mix until homogeneous. Thirty-two, placed samples on ice and proceeded immediately to the next step.

RNA End Repair

First, PNK Enzyme master mix was prepared according to Table 8 below in a fresh 1.5 mL LoBind tube. Note: Included 3% excess volume to correct for pipetting losses.

TABLE 8

| PNK Enzyme master mix (per sample) | |
| --- | --- |
| Reagent | Volume (µL) |
| PNK Buffer | 76 |
| RNase Inhibitor | 1 |
| PNK Enzyme | 3 |
| Total: | 80 |

Second, moved all IP tubes from ice to DynaMag-2 magnet and allowed at least 1 minute for bead separation. Third, removed and discarded supernatant. Forth, spin all samples in mini-centrifuge for 3 seconds. Fifth, place samples back on magnet and allow 1 minute for bead separation. Sixth, pipetted and discarded any excess liquid without disturbing beads. Seventh, added 80 µL of PNK Enzyme master mix to each IP tube. Pipette to mix. Eighth, incubated in thermomixer at 37° C. for 20 minutes with interval mixing at 1,200 rpm.

Second Immunoprecipitation Wash

First, when IP RNA end repair was complete, removed tubes from Thermomixer and added 500 µL cold HSB directly to samples. Second, inverted mix until homogeneous. Third, placed IP tubes on DynaMag-2 magnet to separate beads. Fourth, allowed at least 1 minute for bead separation. Fifth, when separation was complete and liquid was transparent, carefully aspirated and discarded supernatant without disturbing beads. Sixth, removed IP tubes from magnet. Seventh, added 500 µL cold 1× NoS Buffer. Eighth, inverted mix until homogeneous. Ninth, separated beads on magnet and remove supernatant without disturbing beads. Tenth, removed IP tubes from magnet. Eleventh, added 500 µL cold 1× NoS Buffer. Twelfth, inverted mix until homogeneous. Thirteenth, separated beads on magnet and removed supernatant without disturbing beads. Fourteenth, spun all IP samples in mini-centrifuge for 3 seconds. Fifteenth, placed samples back on magnet and allowed 1 minute for bead separation. Sixteenth, pipetted and discarded any excess liquid without disturbing beads. Seventeenth, removed IP tubes from magnet. Eighteenth, added 500 µL cold 1× NoS Buffer. Nineteenth, inverted mix until homogeneous. Twentieth, placed samples on ice and proceed immediately to the next step.

Barcode Chimeric Ligation

First, Chimeric Ligation master mix was prepared according to Table 9 in a fresh 1.5 mL LoBind tube. Note: Included 3% excess volume to correct for pipetting losses. Note: RNA Ligation Buffer was very viscous, and the master mix required thorough mixing.

TABLE 9

| Chimeric Ligation master mix (per sample) | |
|---|---|
| Reagent | Volume (µL) |
| Molecular Biology Grade Water | 43 |
| RNA Ligation Buffer | 94 |
| RNase Inhibitor | 2 |
| T4 Ligase | 11 |
| Total: | 150 |

Second, moved all IP tubes from ice to DynaMag-2 magnet and allowed at least 1 minute for bead separation. Third, removed and discarded supernatant. Fourth, spun all samples in mini-centrifuge for 3 seconds. Fifth, placed samples back on magnet and allowed 1 minute for bead separation. Sixth, pipetted and discarded any excess liquid without disturbing beads. Seventh, slowly added 150 µL of Chimeric Ligation master mix to each IP tube. Gently pipetted mix until homogenous. Eighth, placed IP tubes on tube rotator for 45 minutes at room temperature. Ninth, separated beads on magnet and remove supernatant without disturbing beads. Tenth, removed IP tubes from magnet. Eleventh, added 500 µL cold 1× HSB Buffer. Twelfth, inverted mix until homogeneous. Thirteenth, separated beads on magnet and remove supernatant without disturbing beads. Fourteenth, added 500 µL cold 1× NoS Buffer. Fifteenth, inverted mix until homogeneous. Sixteenth, separated beads on magnet and remove supernatant without disturbing beads. Seventeenth, repeated steps 12-14 for a total of 2 washes.

Proteinase Digestion of Samples

First, proteinase master mix was prepared according to Table 10 below in a fresh 1.5 mL LoBind tube. Note: Included 3% excess volume to correct for pipetting losses.

TABLE 10

| Proteinase master mix (per sample) | |
|---|---|
| Reagent | Volume (µL) |
| Proteinase Buffer | 110 |
| Proteinase Enzyme | 17 |
| Total: | 127 |

Second, added 127 µL of Proteinase master mix to each sample tube containing IP beads and ensure all beads are submerged. Third, incubated in thermomixer at 37° C. for 20 minutes with interval mixing at 1,200 rpm. Fourth, after completion of first incubation, increased temperature to 50° C. and continued incubation in thermomixer at 50° C. for 20 minutes with interval mixing at 1,200 rpm.

Clean All Samples With Zymo RNA Clean & Concentrator Kit

Preparative Note: Ensure 100% EtOH was added to the RNA Wash Buffer concentrate upon first usage. Preparative Note: Centrifugation steps are done at room temperature.

First, for each sample, all liquid (~125 µL) was transferred from proteinase digestion into fresh, labeled DNA LoBind tubes. This contained the eluted RNA sample. Second, added 250 µL of RNA Binding Buffer to the 125 µL of eluted RNA sample. Pipetted to mix. Third, added 375 µL of 100% ethanol to the tubes. Fourth, pipetted mix thoroughly. Fifth, transferred all liquid (750 µL) to corresponding labeled filter-columns in collection tubes. Sixth, centrifuged at 7,000 × g for 30 seconds. Discarded flow-through. Seventh, added 400 µL of RNA Prep Buffer to each column. Eighth, centrifuged at 7,000 × g for 30 seconds. Discarded flow-through. Ninth, added 480 µL of RNA Wash Buffer to each column. Tenth, centrifuged at 7,000 × g for 30 seconds. Discarded flow-through. Eleventh, repeated steps 10-11 once for a total of 2 washes. Twelfth, placed each spin column in a new collection tube. Discarded used collection tubes. Thirteenth, 'Dry' spun at 10,000 × g for 1 minute to remove any residual ethanol. Fourteenth, transferred each filter-column to a new labeled 1.5 mL LoBind tube. Discarded used collection tubes. Fifteenth, opened columns' caps and allowed to air dry for 3 minutes. Sixteenth, eluted all samples by adding 11 µL of Molecular Biology Grade Water directly to each filter. Seventeenth, incubated at room temperature for 1 minute. Eighteenth, centrifuged at 12,000 × g for 90 seconds. Discarded filter-columns. Note: Elution volume was ~10 µL. Nineteenth, if proceeding to next step, store all samples on ice. IP samples can remain on ice or be frozen until Reverse Transcription and cDNA Adapter Ligation.

Optional Stopping Point: If stopping here, RNA samples should be stored at -80° C.

Next stopping point: ~2 h

Reverse Transcription of Sample Reagent Preparation

First, for each IP RNA sample, 9 µL was transferred into a new, labeled 0.2 mL strip tube. Second, added 1.5 µL of ABC RT Primer into RNA. Third, mixed, and spun all samples in mini-centrifuge for 5 seconds to draw all liquid to the bottom of the tube. Fourth, incubated at 65° C. for 2 minutes in thermal cycler with the lid preheated to 70° C. Fifth, after incubation, immediately transferred to ice for 1 minute. Sixth, adjusted the thermal cycler block temperature to 54° C. - 20 minutes (with lid set to 65° C.).

Reverse Transcription of RNA

First, Reverse Transcription Master Mix was prepared according to Table 11 in a fresh 1.5 mL LoBind tube. Second, pipetted sample up and down 10 times to mix. Third, stored samples on ice until use. Note: Included 3% excess volume to correct for pipetting losses.

TABLE 11

| Reverse Transcription Master-Mix (per sample) | |
| --- | --- |
| Component | Volume (μL) |
| RT Buffer | 9.2 |
| RNase Inhibitor | 0.2 |
| Superscript III | 0.6 |
| Total: | 10 |

Fourth, added 10 μL of the Reverse Transcription Master Mix to each sample leaving samples on ice. Pipetted to mix. Fifth, spun samples in mini-centrifuge for 5 seconds to draw all liquid to the bottom of the tube. Sixth, immediately incubated samples at 54° C. for 20 minutes in thermal cycler with the lid at 65° C. Seventh, after incubation, immediately placed samples on ice. Eighth, adjusted thermal cycler block temperature to 37° C. - 15 minutes (with lid set to 45° C.).

cDNA End Repair of Samples

First, 2.5 μL of ExoSap-IT was added to each sample. Second, spun samples in mini-centrifuge for 5 seconds to draw all liquid to the bottom of the tube. Third, incubated in thermal cycler at 37° C. for 15 minutes with the lid at 45° C. Fourth, removed the strip-tube and place samples on ice. Fifth, adjusted thermal cycler block to 70° C. – 10 minutes (with lid set to 75° C.). Sixth, added 1 μL of 0.5 M EDTA (pH 8) to each sample. Seventh, pipetted samples up and down gently 5 times to mix. Eighth, added 3 μL of 1 M NaOH to each sample. Ninth, pipetted samples up and down gently 5 times to mix. Tenth, incubated tubes at 70° C. for 10 minutes in thermal cycler with the lid at 75° C. Eleventh, placed strip-tube on ice for 10 seconds. Twelfth, added 3 μL of 1 M HCl to each sample. Thirteenth, proceeded immediately to the next step.

cDNA Sample Bead Cleanup

Preparation Note: Thawed ssDNA Adapter and ssDNA Ligation Buffer at room temperature until completely melted then store ssDNA Adapter on ice and ssDNA Ligation Buffer at room temperature. Preparation Note: Prepared fresh 80% Ethanol in Molecular Biology Grade water in a fresh 50 mL tube if was not done previously. Store at room temperature for up to 1 week. Keep tube closed tightly.

First, Silane beads out of 4° C. were taken and resuspended until homogeneous. Second, washed Silane beads prior to addition to samples. Third, for each cDNA sample, transferred 5 μL of Silane beads to a new 1.5 mL DNA LoBind tube (e.g. for 4 samples transfer 20 μL of Silane beads). Fourth, added 5× volume of Bead Binding Buffer (e.g. for 4 samples add 100 μL buffer to 20 μL of Silane beads). Pipetted up and down to mix until sample was homogeneous. Fifth, placed tube on DynaMag-2 magnet. When separation was complete and supernatant was clear, carefully aspirated and discarded supernatant without disturbing beads. Sixth, removed tube from magnet. Seventh, resuspended Silane beads in 93 μL of Bead Binding Buffer per sample. Eighth, pipetted up and down until beads are fully resuspended. Ninth, added 90 μL of washed Silane beads to each cDNA sample. Tenth, pipetted up and down to mix until sample is homogeneous. Eleventh, added 90 μL of 100% EtOH to each cDNA sample. Twelfth, pipetted mix until homogeneous. Thirteenth, incubated at room temperature for 10 minutes, with pipette mixing every 5 minutes. Fourteenth, moved samples to fresh strip tube: placed a new, labeled 0.2 mL strip tube on 96-well magnet and transferred sample from old to new strip tube. Fifteenth, allowed to incubate for 1 minute or until separation was complete and liquid was transparent. Sixteenth, carefully discarded supernatant without disturbing beads. Seventeenth, added 150 μL of 80% EtOH, Eighteenth, moved samples to different positions on magnet to wash thoroughly. Nineteenth, added an additional 150 μL of 80% EtOH. Twentieth, incubated on magnet for 30 seconds until separation was completed and supernatant was transparent. Twenty-first, carefully aspirated and discarded all supernatant while on magnet. Twenty-second, repeated steps 17-21 once for a total of two washes. Twenty-third, capped samples were spun in mini-centrifuge for 5 seconds to draw all liquid to the bottom of the tube. Twenty-fourth, placed tube back on 96-well magnet. Twenty-fifth, incubated on magnet for 10 seconds until separation was complete and supernatant was transparent. Twenty-sixth, using fine tips, aspirated and discarded all residual liquid without disturbing beads while on magnet. Twenty-seventh, allowed beads to air dry for 5 minutes or until beads no longer appeared wet and shiny. Note: Do not over dry samples. Twenty-eighth, once completely dry, carefully removed tubes from magnet. Twenty-ninth, resuspended beads in 2.5 μL of ssDNA Adapter. Thirtieth, pipetted to mix until homogeneous. Thirty-first, incubated in thermal cycler at 70° C. for 2 minutes with the lid at 75° C. Thirty-second, following incubation, immediately place on ice for 1 minute.

cDNA Ligation on Beads

First, cDNA Ligation master mix was prepared according to Table 12 in a fresh 1.5 mL LoBind tube. Pipetted mix to combine (do not vortex). Used immediately. Note: Included 3% excess volume to correct for pipetting losses.

TABLE 12

| cDNA Ligation Master Mix (per sample) | |
| --- | --- |
| Component | Volume (μL) |
| ssDNA Ligation Buffer | 6.5 |
| T4 Ligase | 1 |
| Deadenylase | 0.3 |
| Total: | 7.8 |

Second, 7.8 μL of cDNA Ligation master mix was slowly added to each sample from previous section cDNA Bead Clean Up) and pipetted mix until homogeneous. Third, incubated at room temperature overnight on a tube rotator.

Procedure

Ligated cDNA Sample Cleanup

First, ligated-cDNA samples from tube rotator was obtained. Second, to each cDNA sample, added 5 µL of Bead Elution Buffer. Third, added 45 µL of Bead Binding Buffer. Pipetted to mix. Fourth, added 45 µL of 100% EtOH to each sample and pipette mix until homogeneous. Fifth, incubated at room temperature for 10 minutes, with pipette mixing every 5 minutes. Sixth, placed strip-tube on 96-well magnet and allowed to incubate for 1 minute or until separation was complete and liquid was transparent. Seventh, carefully aspirated and discarded supernatant without disturbing beads. Eighth, added 150 µL of 80% EtOH without disturbing beads. Ninth, moved samples to different positions on magnet to wash thoroughly. Tenth, carefully added an additional 150 µL of 80% EtOH. Eleventh, incubated on magnet for 30 seconds or until separation was complete and supernatant was transparent. Twelfth, carefully aspirated and discarded supernatant. Thirteenth, repeated steps 7-11 for a total of two washes. Fourteenth, spun capped samples in mini-centrifuge for 3 seconds to draw all liquid to the bottom of the tube. Fifteenth, placed tube back on 96-well magnet. Sixteenth, incubated on magnet for 30 seconds or until separation was complete and supernatant was transparent. Seventeenth, while on magnet, aspirated and discarded all residual liquid without disturbing beads. Eighteenth, allowed beads to air dry for 5 minutes or until beads no longer appear wet and shiny. Nineteenth, once completely dry, carefully removed tubes from magnet. Twentieth, added 25 µL Bead Elution Buffer to each sample. Twenty-one, pipetted up and down to mix until sample was homogeneous. Twenty-two, incubated for 5 minutes at room temperature. Twenty-third, after incubation, moved tubes to 96-well magnet. Twenty-fourth, incubated on magnet for 30 seconds until separation was complete and supernatant was transparent. Twenty-fifth, transferred supernatant (containing eluted cDNA) to new 0.2 mL strip tubes.

Optional Stopping Point: If stopping here, eluted cDNA samples should be stored at -80° C. Next stopping point: ~2 hrs cDNA Sample Quantification by qPCR First, qPCR master mix was prepared for the appropriate number of reactions according to Table 13 in a fresh 1.5 mL LoBind tube. Note: Included 3% excess volume to correct for pipetting losses.

TABLE 13

| qPCR quantification master mix (per sample) | |
| --- | --- |
| Component | Volume (µL) |
| NEB LUNA Universal qPCR 2× Master Mix | 5 |
| qPCR Primers | 4 |
| Total: | 9 |

Second, obtained and labeled a 96- or 384-well qPCR reaction plate. Third, added 1 µL of eluted cDNA samples to 9 µL of Molecular Biology Grade Water for a 1:10 dilution. Fourth, added 9 µL of qPCR master mix into all assay wells on ice. Fifth, added 1 µL of each diluted cDNA (or water for negative controls) into the designated well. Note: Stored remaining diluted cDNA samples on ice until PCR in the next section. Sixth, covered the plate with a MicroAmp adhesive film and sealed with MicroAmp adhesive film applicator. Seventh, spun plate at 3,000 × g for 1 minute. Eighth, qPCR assay was run according to the user manual for the specific instrument with ran parameters appropriate for SYBR. Note: For example, for the StepOnePlus qPCR system the appropriate program was: 95° C. − 30 sec, (95° C. − 10 sec, 65° C. − 30 sec) × 32 cycles; No melting curve. Ninth, recorded qPCR Ct values for all samples.

Tenth, set threshold to 0.5 – this recommendation was for StepOnePlus System. Note: Typical acceptable Ct values range from 10 to 23. For robust estimation, Ct values for samples should be ≥ 10. If values are below 9, dilute the 1:10 diluted cDNA an additional 10-fold, and re-perform qPCR using the 1:100 diluted cDNA.

PCR Amplification of cDNA and Dual Index Addition

First, Index primers were thawed at room temperature until fully melted. Shook to mix and spun in mini-centrifuge for 3 seconds. Stored on ice until use. Second, prepared PCR amplification reaction mix according to Table 14 in fresh 0.2 mL PCR strip-tubes. Kept tubes on ice. Note: If samples are going to be multiplexed during high-throughput sequencing, ensure that all samples to be pooled together have a unique combination of indexing primers.

TABLE 14

| PCR amplification reaction mix contents (prepare individually for each sample) – Note - can use traditional Illumina index primers | |
| --- | --- |
| Component | Volume (µL) |
| Ligated cDNA | 16 |
| 501 Index Primer | 2 |
| 701 Index Primer | 2 |
| PCR mix | 20 |
| Total: | 40 |

Third, pipetted mix to combine. Fourth, spun samples in mini-centrifuge for 3 seconds to draw all liquid to the bottom of the tube. Fifth, kept samples on ice. Sixth, referred to Ct values recorded to calculate the appropriate number of cycles for each sample. Used formula to calculate N = Ct − 6, where N is the number of cycles performed using the second (two-step) cycling conditions: N + 6 = Total cycles = Ct. Note: e.g. If Ct = 13.1, then N = 7 and Total number of PCR cycles equal 13 (6+7).

Seventh, PCR for the specific number of cycles calculated for each sample was ran according to the PCR program shown in Table 15.

TABLE 15

| PCR Amplification program | | |
| --- | --- | --- |
| Temperature | Time | Cycles |
| 98° C. | 30 seconds | |
| 98° C. | 15 seconds | 6 |
| 70° C. | 30 seconds | |
| 72° C. | 40 seconds | |

| Extra N cycles (N = Ct value − 6) | | |
|---|---|---|
| 98° C. | 15 seconds | N* |
| 72° C. | 45 seconds | |
| 72° C. | 1 minute | |
| 4° C. | ∞ | |
| Total number of PCR cycles | | 6+N |

*N should be ≥ 1 and < 14.

Eighth, samples were immediately on ice to cool following PCR amplification.

AMPure Library PCR Product Cleanup

Preparative Note: Allowed AMPure XP beads to equilibrate at room temperature for 5 minutes.

First, AMPure XP beads were manually shook or vortexed to resuspend the sample until homogeneous. Second, added 60 µL of AMPure XP beads into each 40 µL PCR reaction. Third, pipetted to mix until sample is homogeneous. Fourth, incubated at room temperature for 10 minutes, with pipette mixing every 5 minutes. Fifth, placed strip-tube on 96-well magnet and allowed to incubate for 1 minute or until separation was complete and liquid was transparent. Sixth, carefully aspirated and discarded supernatant without disturbing beads. Seventh, added 150 µL of 80% EtOH without disturbing beads. Eighth, moved samples to different positions on magnet to wash thoroughly. Ninth, carefully added an additional 150 µL of 80% EtOH. Tenth, incubated on magnet for 30 seconds or until separation was complete and supernatant was transparent. Eleventh, carefully aspirated and discarded supernatant. Twelfth, repeated steps 7-11 for a total of two washes. Thirteenth, spun capped samples in mini-centrifuge for 3 seconds to draw all liquid to the bottom of the tube. Fourteenth, placed tube back on 96-well magnet. Fifteenth, incubated on magnet for 30 seconds or until separation was complete and supernatant was transparent. Sixteenth, while on magnet, aspirated and discarded all residual liquid without disturbing beads. Seventeenth, allowed beads to air dry for 5 minutes or until beads no longer appeared wet and shiny. Eighteenth, once completely dry, carefully removed tubes from magnet. Nineteenth, added 20 µL Molecular Biology Grade Water to each sample. Twentieth, pipetted mix until sample is homogeneous. Twenty-first, incubated for 5 minutes at room temperature. Twenty-second, transferred the 20 µL of eluted sample to new strip-tube. Twenty-third, analyze library length and concentration via Agilent Tapestation. Twenty-fourth, if adapter dimer was present, preform an agarose gel extraction for a DNA 200-400 nts in length and retapestation. Twenty-fifth, libraries were sequenced on an Illumina Nextseq 2000. Twenty-sixth, sequencing reads were mapped to the human genome, hg38 using STAR. Twenty-seventh, reads were split into each barcode/RBP computationally using sequences in Table 1.

Figure 6:
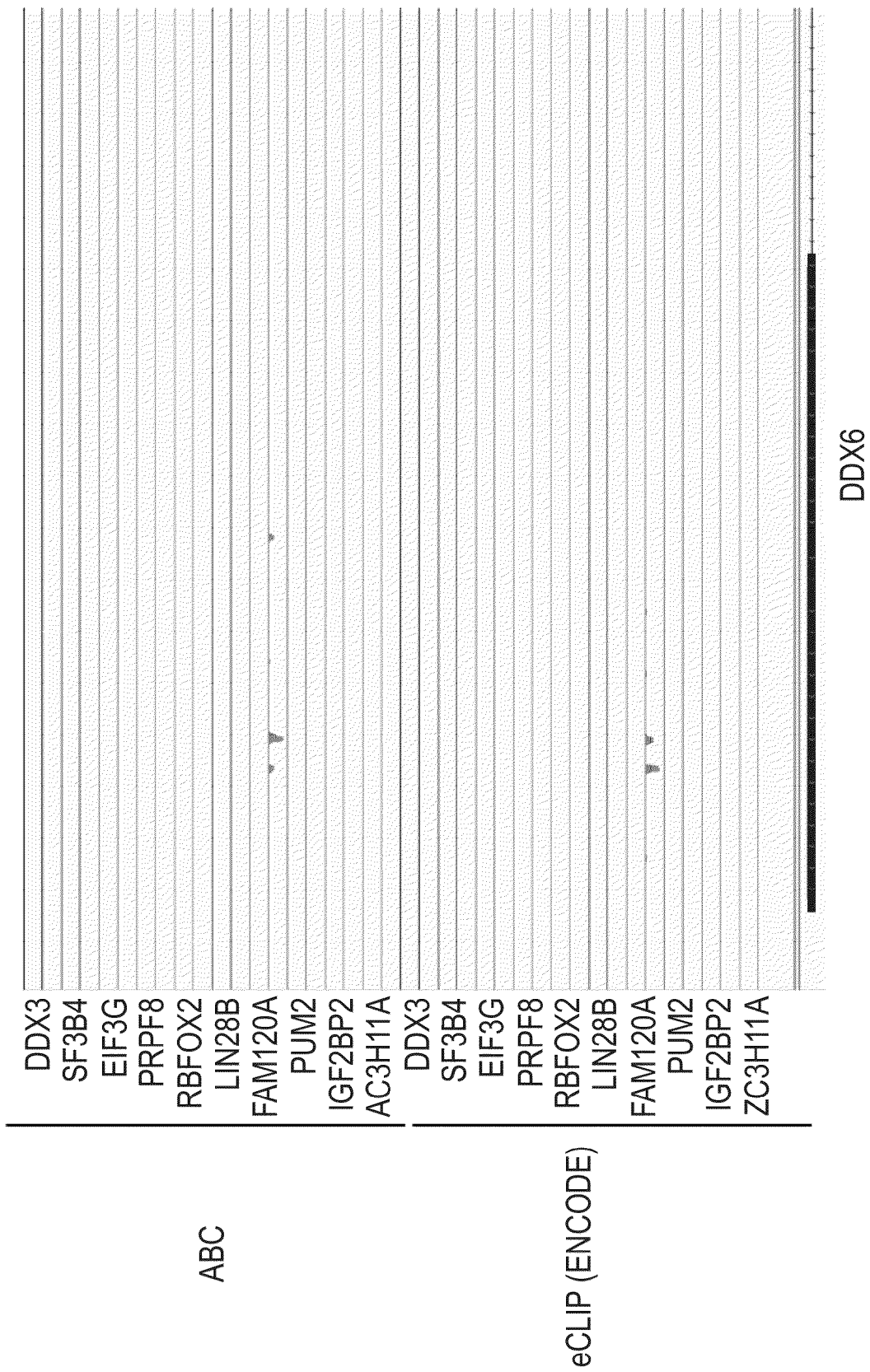
FIG. 6 illustrates a genome view of various RNA binding proteins and their binding to the 3'UTR region of the DDX6 RNA highlighting a RBFOX2 binding site. A comparison of the detected binding between embodiments of the current methods (ABC) and prior methods (eCLIP) is shown.
Figure 7:
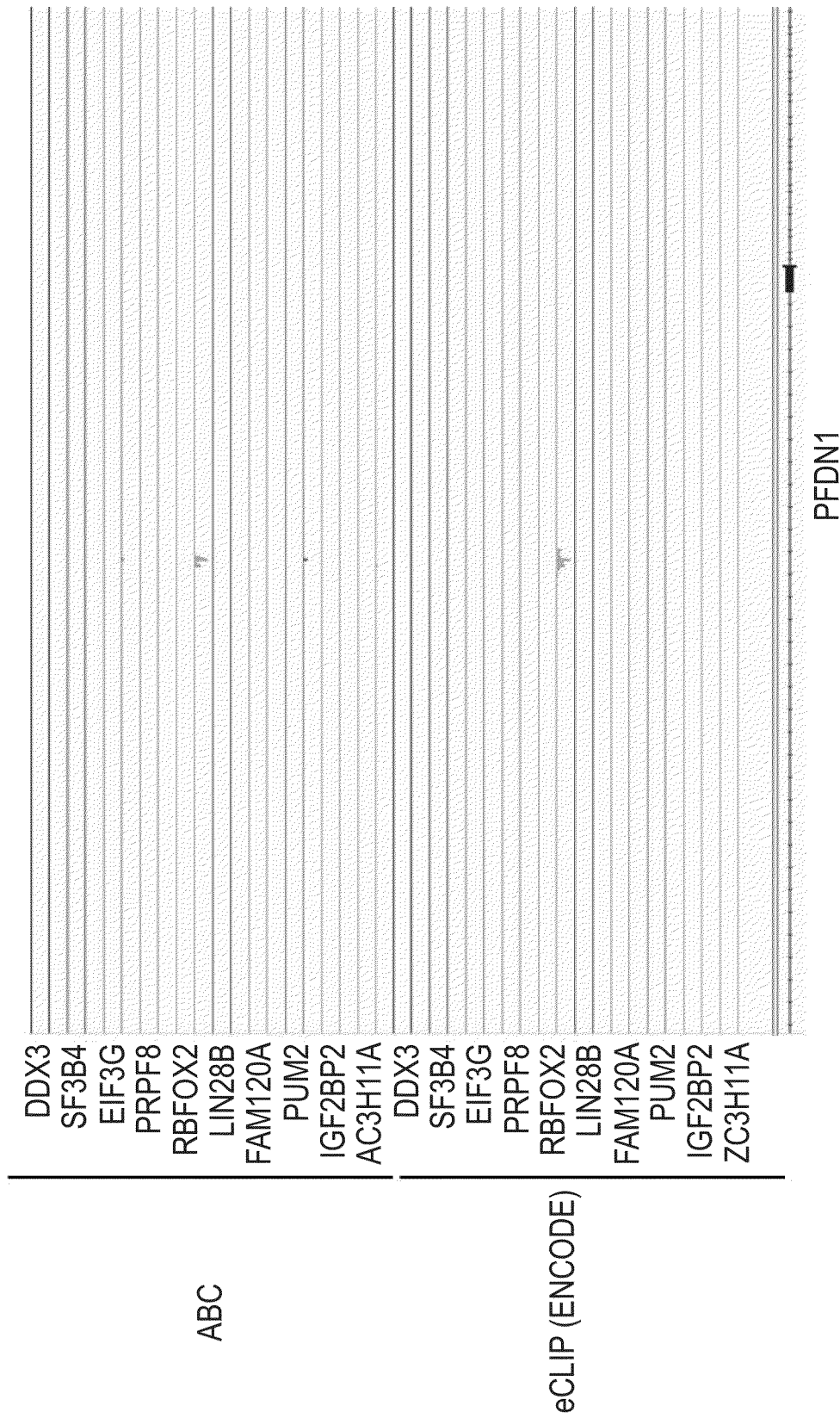
FIG. 7 illustrates a genome view of various RNA binding proteins and their binding to the intronic region of the PFDN1 RNA highlighting a RBFOX2 binding site. A comparison of the detected binding between embodiments of the current methods (ABC) and prior methods (eCLIP) is shown.
Figure 8:
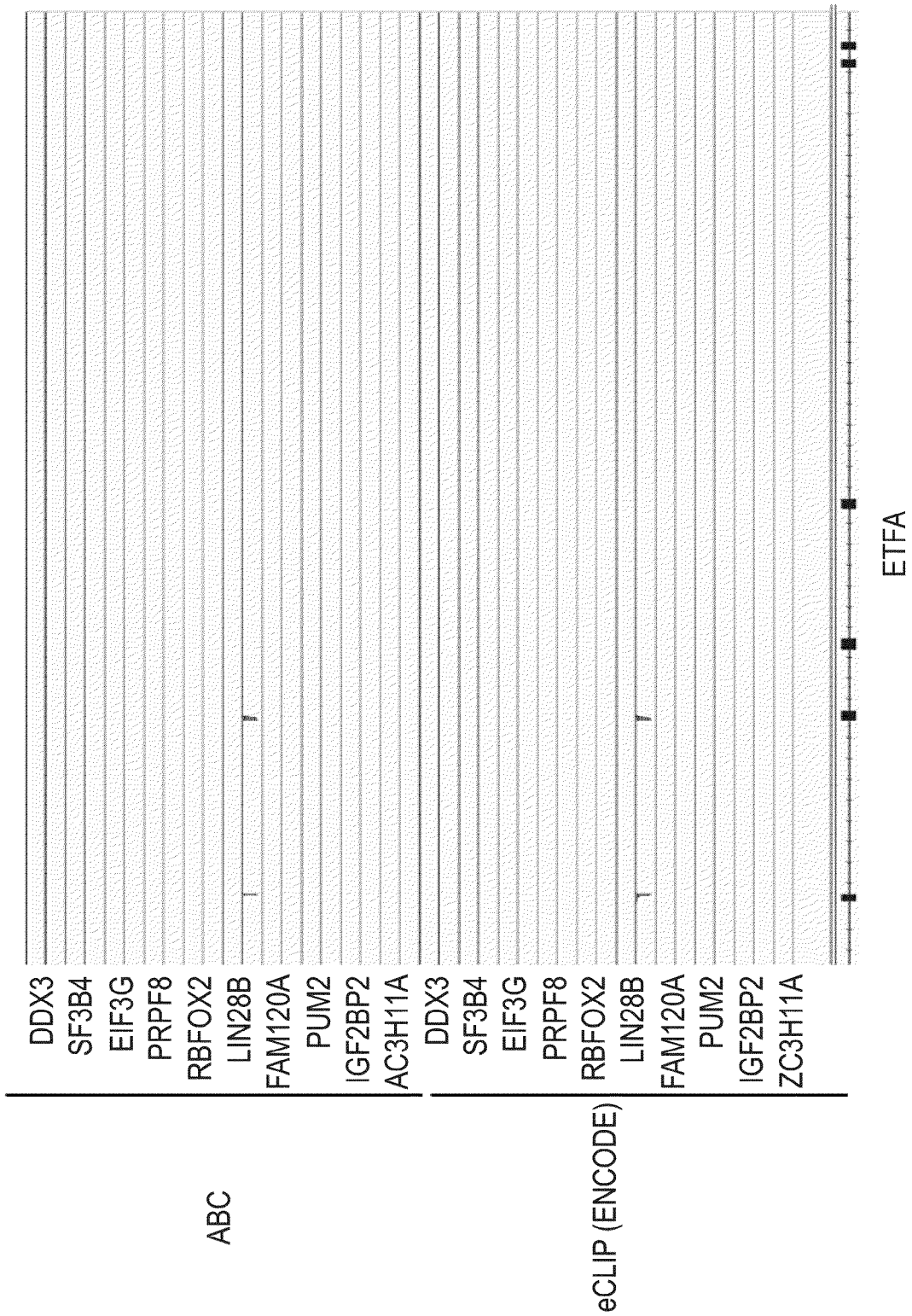
FIG. 8 illustrates a genome view of various RNA binding proteins and their binding to two exons of the ETFA RNA highlighting a LIN28B binding site. A comparison of the detected binding between embodiments of the current methods (ABC) and prior methods (eCLIP) is shown.

FIGS. 7-9 illustrates results of the protocol described above. For FIG. 6, the genome view of DDX6 highlighting a FAM120A binding site. Tracks are from a single antibody chimera (ABC) experiment with 10 different barcoded antibodies that have been demultiplexed compared to 10 separate eCLIP experiments downloaded from the ENCODE database. ABC was performed in HEK293 cells and eCLIP in K562 cells. For FIG. 7, the same data as FIG. 7, but a genome view of the intronic region of PFDN1 highlighting a RBFOX2 binding site. For FIG. 8, the same data as FIG. 6, but a genome view of the exonic region of ETFA highlighting a LIN28B binding site.

Example 3

This example illustrates a protocol for a bead barcoded experiment according to an embodiment of the disclosure. The buffers described below are the same as mentioned above with respect to Example 2.

TABLE 16

| | Barcode Sequence | |
|---|---|---|
| RBP | Barcode Sequence | SEQ ID NO |
| RBFOX2 | /5Phos/ ATTACTCGNNNNNNNNNAGATCGGAA-GAGCGTCGTGT/3AmMO/ | 17 |

TABLE 17

| | Barcode Sequence | |
|---|---|---|
| RBP | Barcode Sequence | SEQ ID NO |
| ZC3H11A | /5Phos/ NNNNNATCACAGATCGGAA-GAGCGTCGTGT/3AmMO/ | 18 |
| RBFOX2 | /5Phos/ NNNNNCGATGAGATCGGAA-GAGCGTCGTGT/3AmMO/ | 19 |
| PUM2 | /5Phos/ NNNNNTTAGGAGATCGGAA-GAGCGTCGTGT/3AmMO/ | 20 |
| IGF2BP2 | /5Phos/ NNNNNTGACCAGATCGGAA-GAGCGTCGTGT/3AmMO/ | 21 |
| SF3B4 | /5Phos/ NNNNNACAGTAGATCGGAA-GAGCGTCGTGT/3AmMO/ | 22 |
| PRPF8 | /5Phos/ NNNNNGCCAAAGATCGGAA-GAGCGTCGTGT/3AmMO/ | 23 |
| YTHDF2 | /5Phos/ NNNNNCAGATAGATCGGAA-GAGCGTCGTGT/3AmMO/ | 24 |
| U2AF2 | /5Phos/ NNNNNACTTGAGATCGGAA-GAGCGTCGTGT/3AmMO/ | 25 |
| FAM120-A | /5Phos/ NNNNNGATCAAGATCGGAA-GAGCGTCGTGT/3AmMO/ | 26 |
| LIN28B | /5Phos/ NNNNNTAGCTAGATCGGAA-GAGCGTCGTGT/3AmMO/ | 27 |

TABLE 18

| | Sequence | |
|---|---|---|
| Oligo | Sequence | SEQ ID NO |
| ABC RT Primer | ACACGACGCTCTTCC | 28 |
| ABC i7 Primer | /5Phos/AGATCGGAAGAGCACACGTCTG/3SpC3 | 29 |
| Index Primer 501 | AATGATACGGCGACCACCGAGATCTACACTA-TAGCCTACACTCTTT CCCTACACGACGCTCTTCCGATCT | 30 |
| Index | CAAGCAGAAGACGGCATACGAGATCGAG- | 31 |

TABLE 18-continued

| Oligo | Sequence | SEQ ID NO |
|---|---|---|
| Primer 701 | TAATGTGACTGGAGTTC AGACGTGTGCTCTTCCGATCT | |

TABLE 19

| qPCR Primer | Sequence | SEQ ID NO |
|---|---|---|
| Primer1 | ACACGACGCTCTTCC | 32 |
| Primer2 | /5Phos/AGATCGGAAGAGCACACGTCTG/3SpC3 | 33 |

TABLE 20

| Reagents | | |
|---|---|---|
| Vendor | Part # | Reagent |
| New England Biolabs® | M0331B | 5' Deadenylase |
| New England Biolabs® | M0544B | NEB NEXT® Ultra™ II Q5® Master Mix |
| New England Biolabs® | P8107B | Proteinase K, Molecular Biology Grade |
| New England Biolabs® | M0314B | RNase Inhibitor, Murine |
| New England Biolabs® | M0201B | T4PNK |
| New England Biolabs® | M0437B-BM | T4 RNA Ligase 1 (ssRNA Ligase) |
| ThermoFisher | EP1756-B012 | SuperScript™ III Reverse Transcriptase Suppled with: 5X First-Strand Buffer – 1x 20 ml. Concentration 200 U/µl Pack Size 200 KU |
| ThermoFisher | 11204D | Dynabeads™ M-280 Sheep-A-RABBIT-10 ml |
| ThermoFisher | AM2239-B001 | TURBO™ DNase Supplied with: 10X TURBO™ DNase Buffer - 7× 1.85 ml |
| ThermoFisher | EF0652-B001 | FastAP Thermosensitive AP Supplied with: 10X Buffer for fastAP - 10 × 1.5 ml |
| Click Chemistry Tools | A124-10 | DBCO-PEG4-NHS Ester (10 mg) |
| Click Chemistry Tools | 1251-5 | 6-Azidohexanoic Acid Sulfo-NHS Ester (5 mg) |
| ThermoFisher | 89882 | Zebra™ Spin Desalting Columns, 7K MWCO, 0.5 ml |
| Corning | 21-040-CV | PBS |
| ThermoFisher | AM2295 | RNase 1 |
| ThermoFisher | 87786 | Halt™ Protease Inhibitor Cocktail (100×) |
| ThermoFisher | 75001.10.ml | ExoSAP-IT™ Express PCR Product Cleanup Reagent |
| Bethyl | A301-524A | ZC3H11A |
| Bethyl | A300-864A | RBFOX2 |
| Bethyl | A300-202A | PUM2 |
| MBL | RN008p | IGF2BP2 |
| Bethyl | A303-950A | SF3B4 |
| Bethyl | A303-921A | PRPF8 |
| Aviva | AR-P67917_-P050 | YTHDF2 |
| Bethyl | A303-666A | U2AF2 |
| Bethyl | A303-889 | FAM120A |
| Bethyl | A303-588A | LIN28B |
| Bethyl | A301-755A | EIF3G |
| Bethyl | A300-474A | DDX3 |

Prepare Cell Pellets (UV Crosslinking of Adherent Cells)

For this example, the equipment and materials included the following: UV Crosslinker with 254 nm wavelength UV bulbs, 1x PBS, Standard cell counting system, liquid nitrogen, Trypan blue stain.

Cell Viability Validation (Prior to Crosslinking)

First, Trypan blue stain (Thermo Fisher Scientific, cat. #15250061) or equivalent live cell counting assay was used to valuate cell viability. Next, cell viability was reviewed to be sure it was > 95% to ensure intact RNA. Cells were grown to a proper confluence, in most cases grow cells to 75% confluence.

Wash Cells

First, the spent media was aspirated. Second, wash the plate gently with PBS at room temperature (15 mL for a 15 cm plate). Third, carefully aspirate PBS. Fourth, add enough PBS to just cover the plate (5 mL for a 15 cm plate).

UV Crosslinking

First, the tissue culture plate was placed on leveled ice or on a cooling block pre-chilled to 4° C. Second, the above (plate plus ice or cooling block) was placed into the UV cross-linker. Third, the tissue culture plate lid for cross-linking was removed. Fourth, crosslink at 254-nm UV with an energy setting of 400 mJoules/cm$^2$. Fifth, while keeping the cells on ice, a cell scraper (Corning, cat. #CLS3010-10EA) was used to scrape the plate. Sixth, the cells were transferred to a 50 mL conical tube. Seventh, the plate was washed once with 10 mL of 1 PBS and added to the same 50 mL tube. Eight, gently resuspended until the sample was homogeneous. Ninth, the cell concentration was counted(either with automated cell counter or hemocytometer). Tenth, the 50 mL conical tube was centrifuged at 200 × g for 5 minutes at room temperature. Eleventh, the sample was aspirated and discarded supernatant. Twelfth, the desired amount of PBS for flash freezing was resuspended (typically 10×10$^6$ cells per mL). Thirteenth, the sample was transferred with a desired amount into 1.5 mL Eppendorf Safe-Lock Tubes (typically 1 mL of 10×10$^6$ cells per mL). Fourteenth, the sample was spun down at 200 × g for 5 minutes at room temperature. Fifteenth, the supernatant was aspirated and the cell pellets were frozen quickly by submerging the 1.5 mL Eppendorf tubes completely in liquid nitrogen. Sixteenth, after frozen (at least thirty seconds), the sample was removed from the liquid nitrogen and store at -80° C.

Prepare Bead Conjugates

Prepare Oligo for Conjugation

First, 100 µL 100 µM Oligo in PBS with 10 µL 10 mM Azide-NHS (10x equiv) was mixed. Second, rotated at RT for 2 hours. Third, the exchange zebra column 3X with 300 ul PBS was buffered at 1,500 XG for 1 min. Marked column orientation. Fourth, oligo reaction was added to zebra column, centrifuge 1,500 XG for 1 min, and saved flowthrough in a new epitube (~110 µL).

Conjugate Barcodes Onto Beads

First, resuspend anti-rabbit Dynabeads by vortexing or pipetting up and down several times. Second, transfer 500 µL of beads (enough for 20 samples) into a 1.5 mL Eppendorf tube and place tube on DynaMag-2. Third, Remove the supernatant and wash beads thrice with 500 µL PBS, resuspending beads with each wash. Fourth, remove beads from magnet, resuspend beads in 500 µL PBS, add 1.65 µL DBCO-NHS (10 mM in DMSO), and rotate tube at room temperature for 1 hour. Fifth, place beads on magnet, remove the supernatant, and wash beads thrice with 500 µL PBS, resuspending beads with each wash. Sixth, resuspend beads with 500 uL PBS and split beads into 5 tubes with 100 uL each. Seventh, add 6.65 µL azide labeled oligo-barcodes to each tube and rotate overnight at room temperature. This can be multiple barcodes or all the same sequence and is enough for 4 samples per 100 µL tube. Eighth, add 200 µL of lysis buffer to each tube, place tubes on magnet. Nineth, remove the supernatant, and wash beads twice with 200 uL PBS, resuspending beads with each wash. Tenth, resuspend beads in 200 µL lysis buffer and store at 4C.

Library Prep

Preparation

First, set chiller on sonicator to 4° C. Second, prewarmed Thermomixer to 37° C. Third, set chiller on centrifuge to 4° C.

Procedure

Cell/Tissue Lysis

First, the lysis mix was prepared for each crosslinked cell pellet according to Table 21.

TABLE 21

| Lysis mix (per one pellet of 10 million cells) | |
|---|---|
| Reagent | Volume (µL) |
| Lysis Buffer | 1000 |
| Protease Inhibitor Cocktail | 5 |
| RNase Inhibitor | 10 |
| Total: | 1015 |

Second, the tubes were retrieved containing pellet(s) from −80° C. and quickly 1 mL of cold lysis mix (do not thaw pellets on ice first) was added. Third, gently mixed until sample was fully resuspended. Fourth, cell tubes were placed on ice for 5 minutes. During lysis, periodically pipette mixed tubes slowly. Fifth, transported samples to sonicator. If necessary, transfer to appropriate pre-chilled tubes for sonication equipment. Sixth, sonicated at 4° C. to disrupt chromatin and fragment DNA (see Table 22 below for settings).

TABLE 22

| Sonicator reference settings | | | |
|---|---|---|---|
| Sonicator | Energy setting | Set time | Cycles |
| QSonica Q800R | 75% amplitude | 5 minutes (total time is 10 min) | 30 seconds ON / 30 seconds OFF |

First, RNase-I 50-fold in 1× PBS was diluted. Second, 5 µL of Turbo DNase to each sample on ice was added to the lysed cells. Third, 10 µL of diluted RNase-I to each sample on ice was added. Proceeded immediately to next step. Fourth, incubated in thermomixer at 37° C. for 5 minutes with interval mixing at 1,200 rpm to fragment RNA. Fifth, immediately following incubation, moved all samples to ice for 3 minutes. Sixth, centrifuged samples at 12,000 × g for 3 minutes at 4° C. to pellet cellular debris. Seventh, transferred supernatant (clarified lysate) to fresh labeled 1.5 mL LoBind tubes without disturbing cell pellet. Eighth, left clarified supernatant on ice until Immunoprecipitation as described herein. Ninth, discarded cell pellets.

Preparation

First, the Lysis Buffer was inverted to mix before use. Second, the High-Salt Buffer (HSB) and 25× NoS (No-Salt) Buffer Concentrate was placed at 4° C. overnight to thaw.

Procedure

Coupling primary antibody to barcoded magnetic beads (Repeat for each antibody separately). First, barcoded magnetic Dynabeads anti-rabbit were mixed until homogeneous. Second, transferred 50 µL Dynabeads anti-Rabbit per sample into a fresh 1.5 mL LoBind tube (e.g. for 3 samples use 150 µL of secondary beads). Third, 200 µL of Lysis Buffer (chilled) was added to the tube with secondary beads. Fourth, placed the tube on DynaMag-2 magnet. Fifth, after separation was complete and supernatant was transparent (~ 1 minute), carefully aspirated and discarded the supernatant without disturbing beads. Sixth, the tube from the magnet was removed. Seventh, 500 µL Lysis Buffer (chilled) to the tube was added, closed the tube and inverted mix until homogeneous. Eighth, placed the tube on DynaMag-2 magnet. Ninth, after separation was complete and supernatant was transparent (~ 1 minute), carefully aspirated and discarded supernatant without disturbing beads. Tenth, the tube from the magnet was removed. Eleventh, repeated steps 7-10 once for a total of two washes. Twelfth, 50 µL Lysis Buffer (chilled) per sample was added to the tube. Thirteenth, 5 µg of primary antibody per sample was added to the tube containing washed beads. Fourteenth, placed tube on tube rotator and allowed beads and antibody to couple for 1 hour at room temperature.

Immunoprecipitation (IP)

First, the antibody-coupled magnetic bead tubes was removed from the rotator. Second, to each antibody-coupled magnetic bead tube, 500 µL Lysis Buffer (chilled) was added. Third, inverted mix until homogenous. Fourth, placed tubes on DynaMag-2 magnet to separate beads and allowed at least 1 minute for bead separation. Fifth, when separation was complete and liquid was transparent, carefully aspirated and discarded supernatant without disturbing beads. Sixth, repeated steps 2-5 for a total of 2 washes. Seventh, removed tubes from magnet. Eighth, added 50 µL Lysis Buffer (chilled) per sample to the tubes. Ninth, added 50 uL of each antibody coated bead to the 1 mL of clarified lysate containing fragmented RNA and slowly pipetted to mix until homogeneous. This should total 500 µL of beads when using 10 RBP targets. Tenth, rotated immunoprecipitation tubes containing fragmented RNA and antibody-coupled magnetic beads overnight at 4° C.

Stopping Point: Samples rotate overnight at 4° C. for up to 16 hours

Preparation

First, diluted 25× NoS (No-Salt) Buffer Concentrate to 1× by adding 2 mL of concentrate to 48 mL of water. Second, prewarmed Thermomixer to 37° C. Third, prepared HSB+ (see Table 23).

TABLE 23

| Preparation of HSB+ (per sample) | |
| --- | --- |
| Component | Volume (µL) |
| 8 M LiCl | 50 |
| High-Salt Buffer (HSB) | 450 |
| Total: | 500 |

Procedure

First Immunoprecipitation (IP) Wash

First, placed IP tubes on DynaMag-2 magnet to separate beads. Second, allowed at least 1 minute for bead separation. Third, when separation was complete and liquid was transparent, carefully aspirated and discarded supernatant without disturbing beads. Forth, removed IP tubes from magnet. Fifth, added 500 µL cold HSB. Sixth, inverted mix until homogeneous. Seventh, placed on DynaMag-2 magnet. Eighth, while on magnet, slowly inverted closed tubes as beads start to separate to capture any beads from cap. Ninth, when separation was complete, and liquid was transparent, gently opened tubes and discard supernatant without disturbing beads. Tenth, removed IP tubes from magnet and added 500 µL cold HSB+ (see Table 23). Eleventh, closed tubes well and vortexed for 15 seconds. Twelfth, incubated on tube rotator for 3 min at room temperature. Thirteenth, placed on DynaMag-2 magnet. Fourteenth, while on magnet, slowly inverted closed tubes as beads start to separate to capture any beads from cap. Fifteenth, when separation was complete, and liquid was transparent, gently opened tubes and discarded supernatant without disturbing beads. Sixteenth, repeated steps 5-9 for an additional round of HSB wash. Seventeenth, removed IP tubes from magnet. Eighteenth, added 500 µL cold 1× NoS Buffer. Nineteenth, inverted mix until homogenous. Twentieth, placed on DynaMag-2 magnet. Twenty-first, while on magnet, slowly inverted closed tubes as beads start to separate to capture any beads from cap. Twenty-two, removed IP tubes from magnet. Twenty-third, added 500 µL cold 1× NoS Buffer. Twenty-four, inverted mix until homogeneous. Twenty-five, separated beads on magnet and removed supernatant without disturbing beads. Twenty-six, spin all samples in mini-centrifuge for 3 seconds. Twenty-seven, placed samples back on magnet and allow 1 minute for bead separation. Twenty-eight, pipetted and discarded any excess liquid without disturbing beads. Twenty-nine, removed IP tubes from magnet. Thirtieth, added 500 µL cold 1× NoS Buffer. Thirty-one, inverted to mix until homogeneous. Thirty-two, placed samples on ice and proceeded immediately to the next step.

RNA End Repair

First, PNK Enzyme master mix was prepared according to Table 24 below in a fresh 1.5 mL LoBind tube. Note: Included 3% excess volume to correct for pipetting losses.

TABLE 24

| PNK Enzyme master mix (per sample) | |
| --- | --- |
| Reagent | Volume (µL) |
| PNK Buffer | 76 |
| RNase Inhibitor | 1 |
| PNK Enzyme | 3 |
| Total: | 80 |

Second, moved all IP tubes from ice to DynaMag-2 magnet and allowed at least 1 minute for bead separation. Third, removed and discarded supernatant. Forth, spin all samples in mini-centrifuge for 3 seconds. Fifth, place samples back on magnet and allow 1 minute for bead separation. Sixth, pipetted and discarded any excess liquid without disturbing beads. Seventh, added 80 µL of PNK Enzyme master mix to each IP tube. Pipette to mix. Eighth, incubated in thermomixer at 37° C. for 20 minutes with interval mixing at 1,200 rpm.

Second Immunoprecipitation Wash

First, when IP RNA end repair was complete, removed tubes from Thermomixer and added 500 µL cold HSB directly to samples. Second, inverted mix until homogeneous. Third, placed IP tubes on DynaMag-2 magnet to separate beads. Fourth, allowed at least 1 minute for bead separation. Fifth, when separation was complete and liquid was transparent, carefully aspirated and discarded supernatant without disturbing beads. Sixth, removed IP tubes from magnet. Seventh, added 500 µL cold 1× NoS Buffer. Eighth, inverted mix until homogeneous. Ninth, separated beads on magnet and remove supernatant without disturbing beads. Tenth, removed IP tubes from magnet. Eleventh, added 500 µL cold 1× NoS Buffer. Twelfth, inverted mix until homogeneous. Thirteenth, separated beads on magnet and removed supernatant without disturbing beads. Fourteenth, spun all IP samples in mini-centrifuge for 3 seconds. Fifteenth, placed samples back on magnet and allowed 1 minute for bead separation. Sixteenth, pipetted and discarded any excess liquid without disturbing beads. Seventeenth, removed IP tubes from magnet. Eighteenth, added 500 µL cold 1× NoS Buffer. Nineteenth, inverted mix until homogeneous. Twentieth, placed samples on ice and proceed immediately to the next step.

Barcode Chimeric Ligation

First, Chimeric Ligation master mix was prepared according to Table 25 in a fresh 1.5 mL LoBind tube. Note: Included 3% excess volume to correct for pipetting losses. Note: RNA Ligation Buffer was very viscous, and the master mix required thorough mixing.

TABLE 25

| Chimeric Ligation master mix (per sample) | |
| --- | --- |
| Reagent | Volume (µL) |
| Molecular Biology Grade Water | 43 |
| RNA Ligation Buffer | 94 |
| RNase Inhibitor | 2 |
| T4 Ligase | 11 |
| Total: | 150 |

Second, moved all IP tubes from ice to DynaMag-2 magnet and allowed at least 1 minute for bead separation. Third, removed and discarded supernatant. Fourth, spun all samples in mini-centrifuge for 3 seconds. Fifth, placed samples back on magnet and allowed 1 minute for bead separation. Sixth, pipetted and discarded any excess liquid without disturbing beads. Seventh, slowly added 150 µL of Chimeric Ligation master mix to each IP tube. Gently pipetted mix until homogenous. Eighth, placed IP tubes on tube rotator for 45 minutes at room temperature. Ninth, separated beads on magnet and remove supernatant without disturbing beads. Tenth, removed IP tubes from magnet. Eleventh, added 500 µL cold 1× HSB Buffer. Twelfth, inverted mix until homogeneous. Thirteenth, separated beads on magnet and remove supernatant without disturbing beads. Fourteenth, added 500 µL cold 1× NoS Buffer. Fifteenth, inverted mix until homogeneous. Sixteenth, separated beads on magnet and remove supernatant without disturbing beads. Seventeenth, repeated steps 12-14 for a total of 2 washes.

Proteinase Digestion of Samples

First, proteinase master mix was prepared according to Table 26 below in a fresh 1.5 mL LoBind tube. Note: Included 3% excess volume to correct for pipetting losses.

TABLE 26

| Proteinase master mix (per sample) | |
|---|---|
| Reagent | Volume (µL) |
| Proteinase Buffer | 110 |
| Proteinase Enzyme | 17 |
| Total: | 127 |

Second, added 127 µL of Proteinase master mix to each sample tube containing IP beads and ensure all beads are submerged. Third, incubated in thermomixer at 37° C. for 20 minutes with interval mixing at 1,200 rpm. Fourth, after completion of first incubation, increased temperature to 50° C. and continued incubation in thermomixer at 50° C. for 20 minutes with interval mixing at 1,200 rpm.

Clean All Samples With Silane Beads

First, resuspend silane beads by vortexing or pipetting up and down several times. Second, transfer 10 uL, per sample, of silane beads to a new Eppendorf tube and add 5X volume of Bead Binding Buffer. Mix by pipetting up and down. Third, place tube on magnet and remove supernatant. Fourth, resuspend beads in 558 uL Bead Binding Buffer per sample. Fifth, transfer 540 uL silane beads into the protease treated sample from line along with 532 uL 100% ethanol, pipette to mix. Sixth, incubate solution at room temperature for 10 minutes, mixing samples by pipetting every 5 minutes. Seventh, place tubes on magnet and remove supernatant. Eighth, add 150 uL of 80% ethanol to the beads and mix. Ninth, transfer solutions into a PCR strip tube. Tenth, add an additional 150 uL 80% ethanol, place tubes on magnet, and remove supernatant. Eleventh, repeat steps 8 and 10. Twelfth, allow beads to air dry until they no longer appear wet and shiny. Thirteenth, remove tubes from magnet, add 11 uL water to the beads, mix by pipetting, and incubate at room temperature for 5 minutes. Fourteenth, place tubes on magnet and allow beads to separate. Fifteenth, transfer supernatant into a fresh PCR tube.

Optional Stopping Point: If stopping here, RNA samples should be stored at -80° C.

Next stopping point: ~2 h

Reverse Transcription of Sample Reagent Preparation

First, for each IP RNA sample, 9 µL was transferred into a new, labeled 0.2 mL strip tube. Second, added 1.5 µL of ABC RT Primer into RNA. Third, mixed, and spun all samples in mini-centrifuge for 5 seconds to draw all liquid to the bottom of the tube. Fourth, incubated at 65° C. for 2 minutes in thermal cycler with the lid preheated to 70° C. Fifth, after incubation, immediately transferred to ice for 1 minute. Sixth, adjusted the thermal cycler block temperature to 54° C. – 20 minutes (with lid set to 65° C.).

Reverse Transcription of RNA

First, Reverse Transcription Master Mix was prepared according to Table 27 in a fresh 1.5 mL LoBind tube. Second, pipetted sample up and down 10 times to mix. Third, stored samples on ice until use. Note: Included 3% excess volume to correct for pipetting losses.

TABLE 27

| Reverse Transcription Master-Mix (per sample) | |
|---|---|
| Component | Volume (µL) |
| RT Buffer | 9.2 |
| RNase Inhibitor | 0.2 |
| Superscript III | 0.6 |
| Total: | 10 |

Fourth, added 10 µL of the Reverse Transcription Master Mix to each sample leaving samples on ice. Pipetted to mix. Fifth, spun samples in mini-centrifuge for 5 seconds to draw all liquid to the bottom of the tube. Sixth, immediately incubated samples at 54° C. for 20 minutes in thermal cycler with the lid at 65° C. Seventh, after incubation, immediately placed samples on ice. Eighth, adjusted thermal cycler block temperature to 37° C. - 15 minutes (with lid set to 45° C.).

cDNA End Repair of Samples

First, 2.5 µL of ExoSap-IT was added to each sample. Second, spun samples in mini-centrifuge for 5 seconds to draw all liquid to the bottom of the tube. Third, incubated in thermal cycler at 37° C. for 15 minutes with the lid at 45° C. Fourth, removed the strip-tube and place samples on ice. Fifth, adjusted thermal cycler block to 70° C. – 10 minutes (with lid set to 75° C.). Sixth, added 1 µL of 0.5 M EDTA (pH 8) to each sample. Seventh, pipetted samples up and down gently 5 times to mix. Eighth, added 3 µL of 1 M NaOH to each sample. Ninth, pipetted samples up and down gently 5 times to mix. Tenth, incubated tubes at 70° C. for 10 minutes in thermal cycler with the lid at 75° C. Eleventh, placed strip-tube on ice for 10 seconds. Twelfth, added 3 µL of 1 M HCl to each sample. Thirteenth, proceeded immediately to the next step.

cDNA Sample Bead Cleanup

Preparation Note: Thawed ssDNA Adapter and ssDNA Ligation Buffer at room temperature until completely melted then store ssDNA Adapter on ice and ssDNA Ligation Buffer at room temperature. Preparation Note: Prepared fresh 80% Ethanol in Molecular Biology Grade water in a fresh 50 mL tube if was not done previously. Store at room temperature for up to 1 week. Keep tube closed tightly.

First, Silane beads (provided) out of 4° C. were taken and resuspended until homogeneous. Second, washed Silane beads prior to addition to samples. Third, for each cDNA sample, transferred 5 µL of Silane beads to a new 1.5 mL DNA LoBind tube (e.g. for 4 samples transfer 20 µL of Silane beads). Fourth, added 5× volume of Bead Binding Buffer (e.g. for 4 samples add 100 µL buffer to 20 µL of Silane beads). Pipetted up and down to mix until sample was homogeneous. Fifth, placed tube on DynaMag-2 magnet. When separation was complete and supernatant was clear, carefully aspirated and discarded supernatant without disturbing beads. Sixth, removed tube from magnet. Seventh, resuspended Silane beads in 93 μL of Bead Binding Buffer per sample. Eighth, pipetted up and down until beads are fully resuspended. Ninth, added 90 μL of washed Silane beads to each cDNA sample. Tenth, pipetted up and down to mix until sample is homogeneous. Eleventh, added 90 μL of 100% EtOH to each cDNA sample. Twelfth, pipetted mix until homogeneous. Thirteenth, incubated at room temperature for 10 minutes, with pipette mixing every 5 minutes. Fourteenth, moved samples to fresh strip tube: placed a new, labeled 0.2 mL strip tube on 96-well magnet and transferred sample from old to new strip tube. Fifteenth, allowed to incubate for 1 minute or until separation was complete and liquid was transparent. Sixteenth, carefully discarded supernatant without disturbing beads. Seventeenth, added 150 μL of 80% EtOH, Eighteenth, moved samples to different positions on magnet to wash thoroughly. Nineteenth, added an additional 150 μL of 80% EtOH. Twentieth, incubated on magnet for 30 seconds until separation was completed and supernatant was transparent. Twenty-first, carefully aspirated and discarded all supernatant while on magnet. Twenty-second, repeated steps 17-21 once for a total of two washes. Twenty-third, capped samples were spun in mini-centrifuge for 5 seconds to draw all liquid to the bottom of the tube. Twenty-fourth, placed tube back on 96-well magnet. Twenty-fifth, incubated on magnet for 10 seconds until separation was complete and supernatant was transparent. Twenty-sixth, using fine tips, aspirated and discarded all residual liquid without disturbing beads while on magnet. Twenty-seventh, allowed beads to air dry for 5 minutes or until beads no longer appeared wet and shiny. Note: Do not over dry samples. Twenty-eighth, once completely dry, carefully removed tubes from magnet. Twenty-ninth, resuspended beads in 2.5 μL of ssDNA Adapter and 7.5uL water. Thirtieth, pipetted to mix until homogeneous. Thirty-first, incubated in thermal cycler at 70° C. for 2 minutes with the lid at 75° C. Thirty-second, following incubation, immediately place on ice for 1 minute.

cDNA Ligation On Beads

First, cDNA Ligation master mix was prepared according to Table 28 in a fresh 1.5 mL LoBind tube. Pipetted mix to combine (do not vortex). Used immediately. Note: Included 3% excess volume to correct for pipetting losses.

TABLE 28

| cDNA Ligation Master Mix (per sample) | |
| --- | --- |
| Component | Volume (μL) |
| ssDNA Ligation Buffer | 26 |
| T4 Ligase | 4 |
| Deadenylase | 1.2 |
| Total: | 31.2 |

Second, 31.2 μL of cDNA Ligation master mix was slowly added to each sample from previous section cDNA Bead Clean Up) and pipetted mix until homogeneous. Third, incubated at room temperature overnight on a tube rotator.

Procedure

Ligated cDNA Sample Cleanup

First, ligated-cDNA samples from tube rotator was obtained. Second, resuspend AMPure XP beads by vortexing or pipetting up and down. Third, add 46.8 uL of AMPure XP beads to each cDNA ligation reaction. Mix by pipetting. Fourth, incubate samples at room temperature for 10 minutes, pipetting up and down every 5 minutes to mix. Fifth, move samples to magnet, allow for the beads the separate and remove supernatant. Sixth, add 150 uL 80% ethanol and move samples across the magnet to wash the beads. Seventh, add 150 uL 80% ethanol to each sample and remove supernatant without disturbing beads. Eighth, repeat steps 6 and 7. Ninth, allow beads to air dry until they no longer appear wet and shiny and remove from magnet. Tenth, add 20 uL water to each sample, mix by pipetting, and incubate at room temperature for 5 minutes. Eleventh, place tube back on magnet and allow beads to separate. Twelfth, transfer supernatant to a fresh PCR tube.

Optional Stopping Point: If stopping here, eluted cDNA samples should be stored at -80° C. Next stopping point: ~2 hrs cDNA Sample Quantification by qPCR First, qPCR master mix was prepared for the appropriate number of reactions according to Table 29 in a fresh 1.5 mL LoBind tube. Note: Included 3% excess volume to correct for pipetting losses.

TABLE 29

| qPCR quantification master mix (per sample) | |
| --- | --- |
| Component | Volume (μL) |
| NEB LUNA® Universal qPCR 2× Master Mix | 5 |
| qPCR Primers | 4 |
| Total: | 9 |

Second, obtained and labeled a 96- or 384-well qPCR reaction plate. Third, added 1 μL of eluted cDNA samples to 9 μL of Molecular Biology Grade Water for a 1:10 dilution. Fourth, added 9 μL of qPCR master mix into all assay wells on ice. Fifth, added 1 μL of each diluted cDNA (or water for negative controls) into the designated well. Note: Stored remaining diluted cDNA samples on ice until PCR in the next section. Sixth, covered the plate with a MicroAmp adhesive film and sealed with MicroAmp adhesive film applicator. Seventh, spun plate at 3,000 × g for 1 minute. Eighth, qPCR assay was run according to the user manual for the specific instrument with ran parameters appropriate for SYBR. Note: For example, for the StepOnePlus qPCR system the appropriate program was: 95° C. – 30 sec, (95° C. – 10 sec, 65° C. – 30 sec) × 32 cycles; No melting curve. Ninth, recorded qPCR Ct values for all samples. Tenth, set threshold to 0.5 – this recommendation was for StepOnePlus System. Note: Typical acceptable Ct values range from 10 to 23. For robust estimation, Ct values for samples should be ≥ 10. If values are below 9, dilute the 1:10 diluted cDNA an additional 10-fold, and re-perform qPCR using the 1:100 diluted cDNA.

PCR Amplification of cDNA and Dual Index Addition

First, Index primers were thawed at room temperature until fully melted. Shook to mix and spun in mini-centrifuge for 3 seconds. Stored on ice until use. Second, prepared PCR amplification reaction mix according to Table 30 in fresh 0.2 mL PCR strip-tubes. Kept tubes on ice. Note: If samples are going to be multiplexed during high-throughput sequencing, ensure that all samples to be pooled together have a unique combination of indexing primers.

TABLE 30

| PCR amplification reaction mix contents (prepare individually for each sample) –Note - can use traditional Illumina index primers | |
|---|---|
| Component | Volume (µL) |
| Ligated cDNA | 16 |
| 501 Index Primer | 2 |
| 701 Index Primer | 2 |
| PCR mix | 20 |
| Total: | 40 |

Third, pipetted mix to combine. Fourth, spun samples in mini-centrifuge for 3 seconds to draw all liquid to the bottom of the tube. Fifth, kept samples on ice. Sixth, referred to Ct values recorded to calculate the appropriate number of cycles for each sample. Used formula to calculate N = Ct - 6, where N is the number of cycles performed using the second (two-step) cycling conditions: N + 6 = Total cycles = Ct. Note: e.g. If Ct = 13.1, then N = 7 and Total number of PCR cycles equal 13 (6+7).

Seventh, PCR for the specific number of cycles calculated for each sample was ran according to the PCR program shown in Table 31.

TABLE 31

| PCR Amplification program | | |
|---|---|---|
| Temperature | Time | Cycles |
| 98° C. | 30 seconds | |
| 98° C. | 15 seconds | 6 |
| 70° C. | 30 seconds | |
| 72° C. | 40 seconds | |
| Extra N cycles (N = Ct value - 6) | | |
| 98° C. | 15 seconds | N* |
| 72° C. | 45 seconds | |
| 72° C. | 1 minute | |
| 4° C. | ∞ | |
| Total number of PCR cycles | | 6+N |

*N should be ≥ 1 and < 14.

Eighth, samples were immediately on ice to cool following PCR amplification.

AMPure Library PCR Product Cleanup

Preparative Note: Allowed AMPure XP beads to equilibrate at room temperature for 5 minutes.

First, AMPure XP beads were manually shook or vortexed to resuspend the sample until homogeneous. Second, added 60 µL of AMPure XP beads into each 40 µL PCR reaction. Third, pipetted to mix until sample is homogeneous. Fourth, incubated at room temperature for 10 minutes, with pipette mixing every 5 minutes. Fifth, placed strip-tube on 96-well magnet and allowed to incubate for 1 minute or until separation was complete and liquid was transparent. Sixth, carefully aspirated and discarded supernatant without disturbing beads. Seventh, added 150 µL of 80% EtOH without disturbing beads. Eighth, moved samples to different positions on magnet to wash thoroughly. Ninth, carefully added an additional 150 µL of 80% EtOH. Tenth, incubated on magnet for 30 seconds or until separation was complete and supernatant was transparent. Eleventh, carefully aspirated and discarded supernatant. Twelfth, repeated steps 7-11 for a total of two washes. Thirteenth, spun capped samples in mini-centrifuge for 3 seconds to draw all liquid to the bottom of the tube. Fourteenth, placed tube back on 96-well magnet. Fifteenth, incubated on magnet for 30 seconds or until separation was complete and supernatant was transparent. Sixteenth, while on magnet, aspirated and discarded all residual liquid without disturbing beads. Seventeenth, allowed beads to air dry for 5 minutes or until beads no longer appeared wet and shiny. Eighteenth, once completely dry, carefully removed tubes from magnet. Nineteenth, added 20 µL Molecular Biology Grade Water to each sample. Twentieth, pipetted mix until sample is homogeneous. Twenty-first, incubated for 5 minutes at room temperature. Twenty-second, transferred the 20 µL of eluted sample to new strip-tube. Twenty-third, analyze library length and concentration via Agilent Tapestation. Twenty-fourth, if adapter dimer was present, preform an agarose gel extraction for a DNA 200-400 nts in length and retapestation. Twenty-fifth, libraries were sequenced on an Illumina Nextseq 2000. Twenty-sixth, sequencing reads were mapped to the human genome, hg38 using STAR. Twenty-seventh, reads were split into each barcode/RBP computationally using sequences in Table 16 or 17.

Figure 9A:
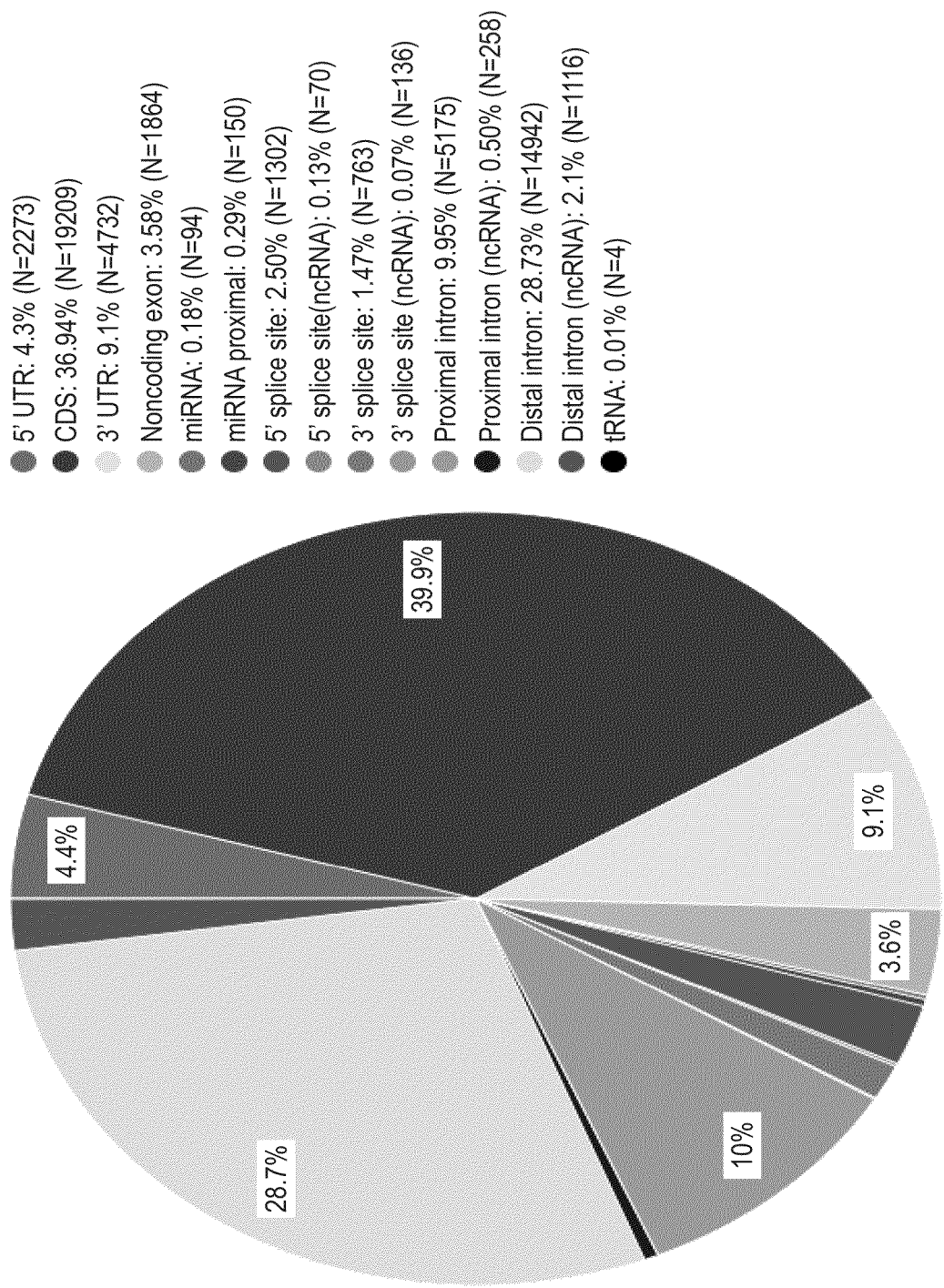
FIG. 9A illustrates a pie chart representing locations of peaks within highlighted RNA features utilizing an antibody conjugated barcode.
Figure 9B:
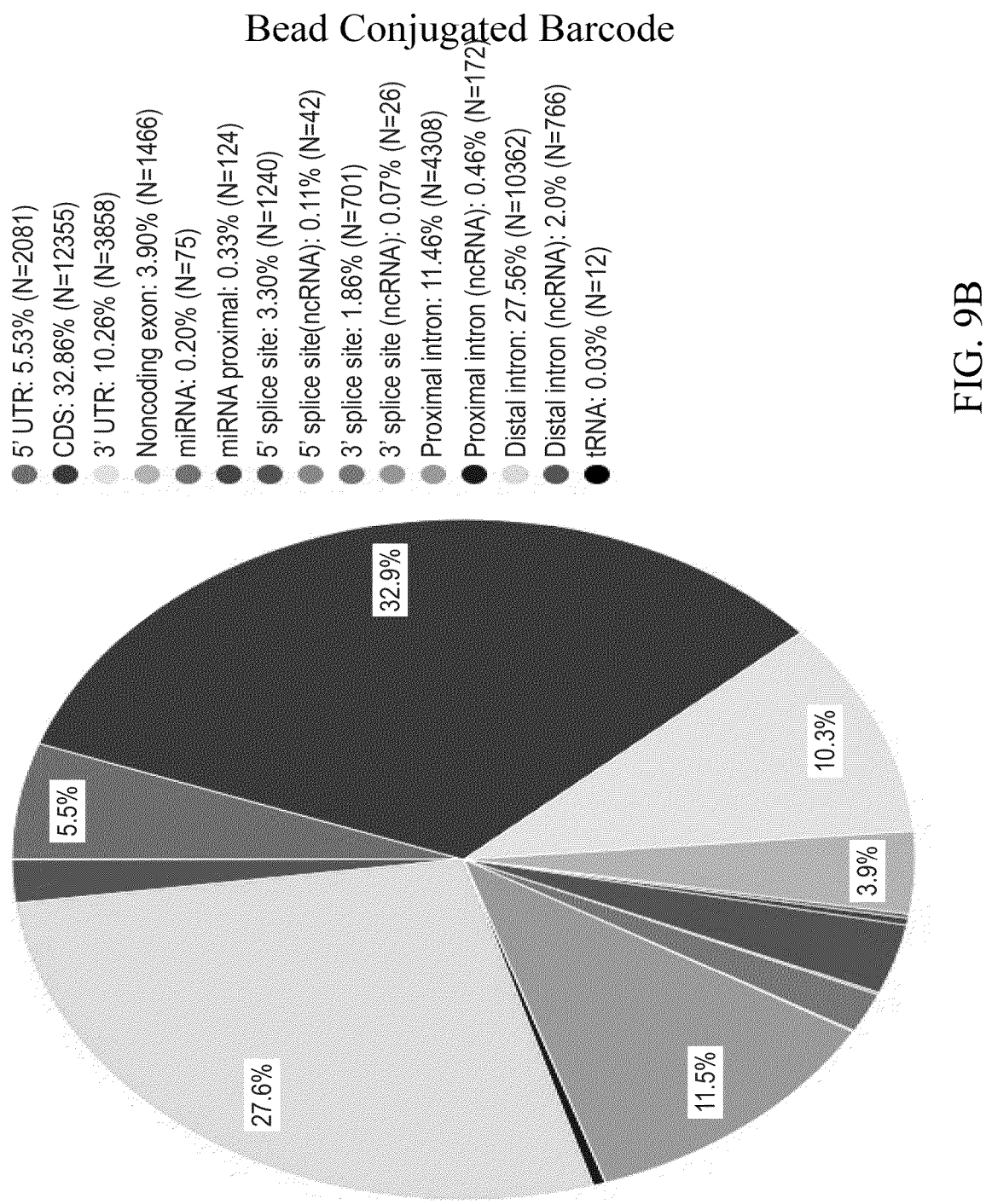
FIG. 9B illustrates a pie chart representing locations of peaks within highlighted RNA features utilizing a bead conjugated barcode.
Figure 10:
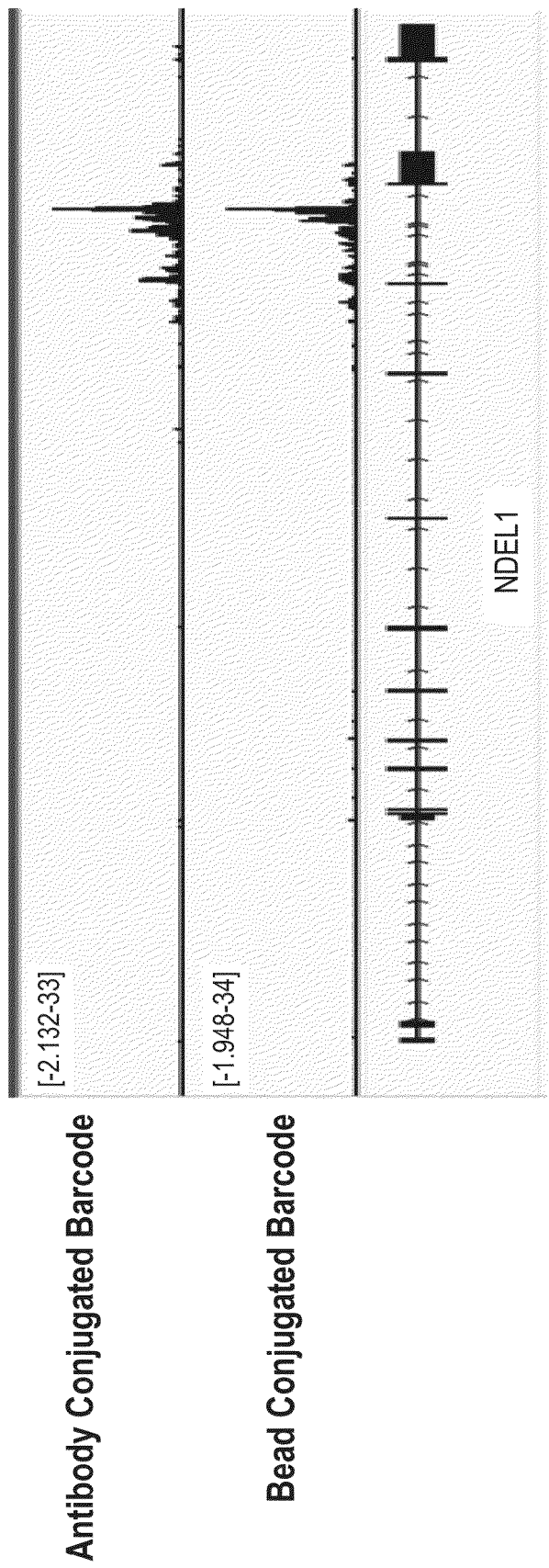
FIG. 10 illustrates a genome view of a RBFOX2 binding site within the intronic region of NDEL1. Both the antibody and bead oligo conjugation methods are displayed.

FIGS. 9A, 9B, and 10 illustrate results of the protocol described above using Table 16. For FIGS. 9A and 9B, the venn diagrams represent to locations of peaks within highlighted RNA features. Data was collected from HEK293T cells. For FIG. 10, the same data as FIG. 7, but a genome view of the intronic region of NDEL1 highlighting a RBFOX2 binding site.

Figure 14:
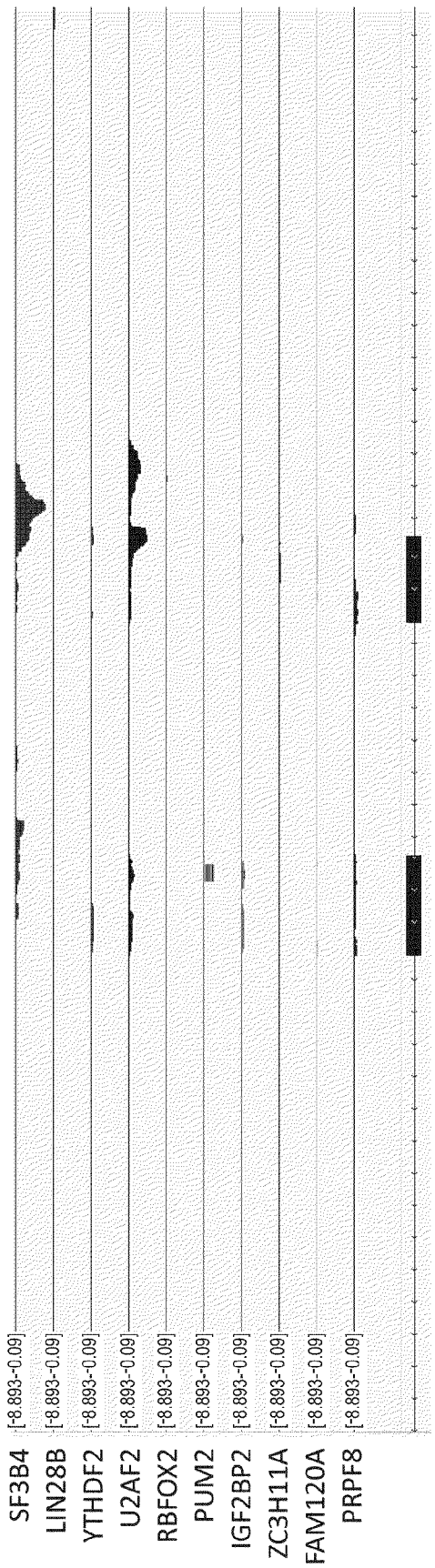
FIG. 14 illustrates a schematic depicting an embodiment of an on bead proximity ligation binding to the intronic region of the MAPK1 RNA, highlighting binding sites for SF3B4 and U2AF2.
Figure 15:
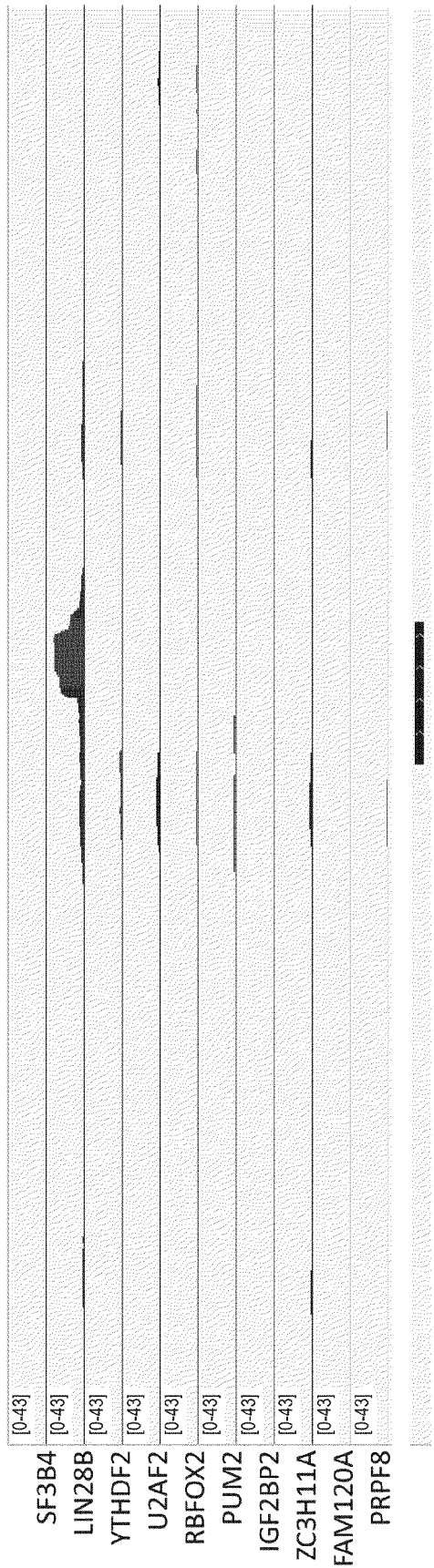
FIG. 15 illustrates a schematic depicting an embodiment of an on bead proximity ligation binding to the noncoding region of the miRNA Let7-d, highlighting a binding site for LIN28B.
Figure 16:
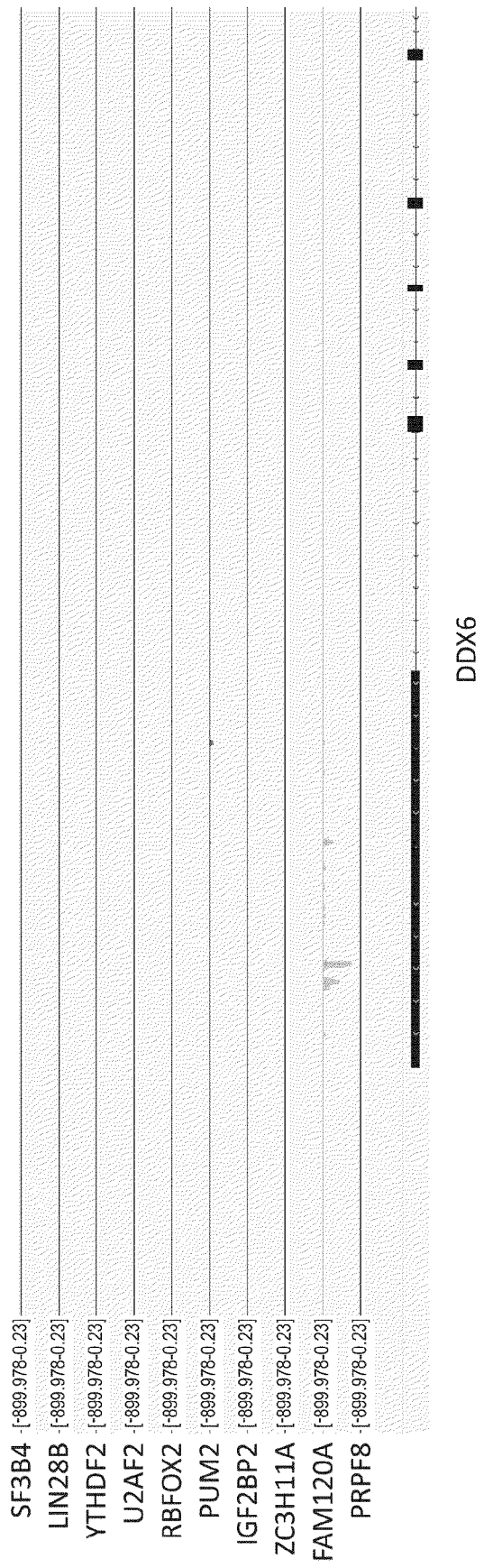
FIG. 16 illustrates a schematic depicting an embodiment of an on bead proximity ligation binding to the 3' UTR region of the DDX6 RNA, highlighting a binding site for FAM120A.
Figure 17:
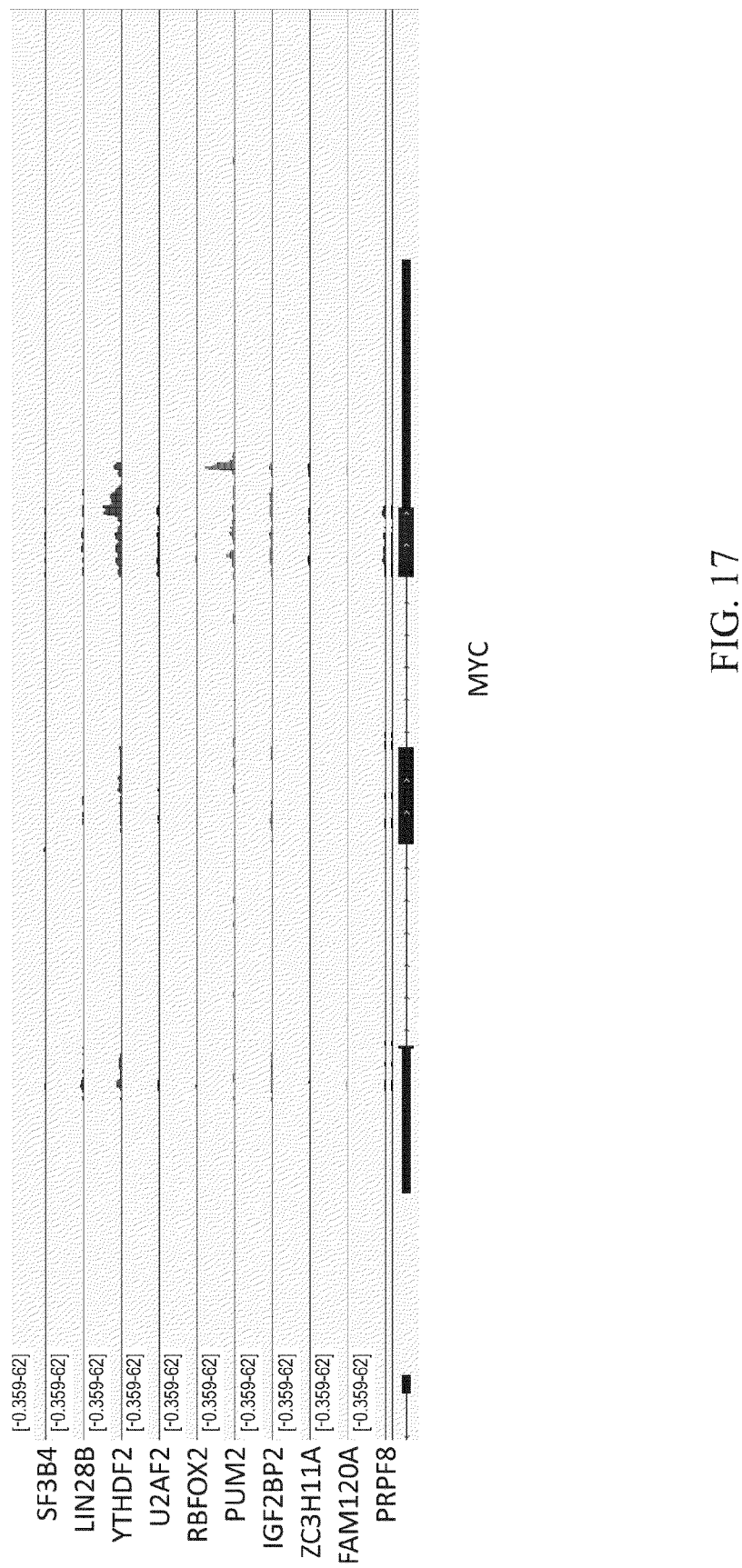
FIG. 17 illustrates a schematic depicting an embodiment of an on bead proximity ligation binding to the 3' UTR region of the MYC RNA, highlighting binding sites for YTHDF2 and PUM2.
Figure 18:
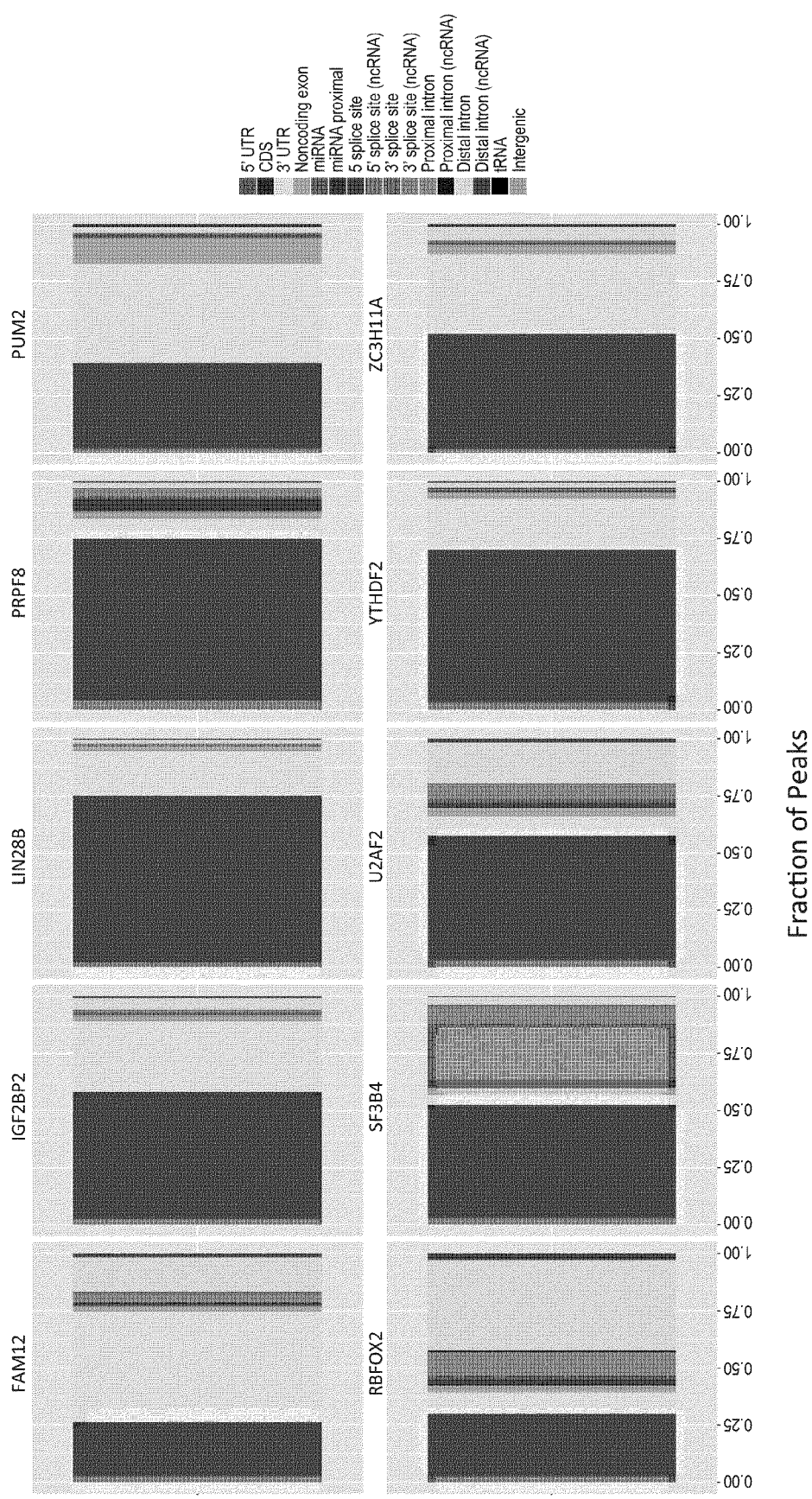
FIG. 18 illustates bar graphs for each RBP within a single experiment and depicts the fraction of peaks identified within different RNA features.

FIGS. 13 through 18 illustrate results of the protocol described above using Table 17 (10 barcodes). FIG. 13 illustrates a schematic diagram depicting an embodiment of a protocol for identifying RNA targets using on bead proximity ligation. FIG. 14 illustrates a schematic depicting an embodiment of an on bead proximity ligation binding to the intronic region of the MAPK1 RNA, highlighting binding sites for SF3B4 and U2AF2. FIG. 15 illustrates a schematic depicting an embodiment of an on bead proximity ligation binding to the noncoding region of the miRNA Let7-d, highlighting a binding site for LIN28B. FIG. 16 illustrates a schematic depicting an embodiment of an on bead proximity ligation binding to the 3' UTR region of the DDX6 RNA, highlighting a binding site for FAM120A. FIG. 17 illustrates a schematic depicting an embodiment of an on bead proximity ligation binding to the 3' UTR region of the MYC RNA, highlighting binding sites for YTHDF2 and PUM2. FIG. 18 illustates bar graphs for each RBP within a single experiment and depicts the fraction of peaks identified within different RNA features.

Example 4

This example is a protocol for amplifying and quantifying an individual barcode from a multiplexed experiment, such as Example 2.

Reagents

LUNA® qPCR master mix (NEB cat #M3003X)
NEB Next® Ultra™ II Q5® Master Mix (NEB cat# M0544S)
AMPure XP Reagent (Beckman cat# A63882)

TABLE 32

| Primer label | Primer Sequence | SEQ ID NO |
|---|---|---|
| BC1_AMP | ACACGACGCTCTTCCGATCTGTGAT | 34 |
| BC2_AMP | ACACGACGCTCTTCCGATCTCATCG | 35 |
| BC3_AMP | ACACGACGCTCTTCCGATCTCCTAA | 36 |
| BC4_AMP | ACACGACGCTCTTCCGATCTGGTCA | 37 |
| BC5_AMP | ACACGACGCTCTTCCGATCTACTGT | 38 |
| BC6_AMP | ACACGACGCTCTTCCGATCTTTGGC | 39 |
| BC7_AMP | ACACGACGCTCTTCCGATCTATCTG | 40 |
| BC8_AMP | ACACGACGCTCTTCCGATCTCAAGT | 41 |
| BC9_AMP | ACACGACGCTCTTCCGATCTTGATC | 42 |
| BC10_AMP | ACACGACGCTCTTCCGATCTAGCTA | 43 |
| BC_AMP_REV | CAGACGTGTGCTCTTCCGATCT | 44 |

Amplification

Mix 1 µl of cDNA from example 3, 0.5uL BCX_AMP primer (100 uM stock in water), 0.5 µL BC_AMP_REV primer (100uM stock in water), and 20 µL NEBNext Ultra PCR master mix. Amplify cDNA with the PCR amplification program of Table 33.

TABLE 33

| Temperature | Time | Cycles |
|---|---|---|
| 98° C. | 30 seconds | |
| 98° C. | 15 seconds | 9 |
| 65° C. | 30 seconds | |
| 72° C. | 40 seconds | |
| 72° C. | 2 minute | |
| 4° C. | ∞ | |

Cleanup

First, 32 µL of AMPure XP beads were added to each PCR reaction and mixed by pipetting. Second, samples were incubated at room temperature for 10 minutes, mixing by pipetting every 5 minutes. Third, samples were placed on a magnetic PCR tube holder and beads were allowed to settle. Fourth, the supernatant was removed and replaced with 150 µL 80% ethanol. Fifth, the PCR tubes were moved around the magnet to facilitate bead movement, allowing for effective washing. Sixth, an additional 150 µL of 80% ethanol was added to each sample. Seventh, all supernatant was carefully removed without disturbing the bead pellet. Eighth, repeat steps 4 through 7 for a second wash. Nineth, after removing the supernatant allow beads to dry until they no longer appear wet and shiny. Tenth, remove tubes from magnet, add 20 µL water to each sample, mix by pipetting, and incubate at room temperature for 5 minutes. Eleventh, place the sample back on magnet and allow beads to settle. Twelfth, transfer supernatant to a fresh PCR tube.

Quantification

First, mix 1 uL of amplified DNA from the cleanup step with 2 uL BCX_AMP primer (1.25 uM stock in water), 2 uL BC_AMP_REV primer (1.25 µM stock in water), and 5 µL Luna qPCR master mix in a qPCR plate. Second, spun plate at 3,000 × g for 1 minute. Third, qPCR assay was run according to the user manual for the specific instrument with ran parameters appropriate for SYBR. Note: For example, for the StepOnePlus qPCR system the appropriate program was: 95° C. – 30 sec, (95° C. – 10 sec, 65° C. – 30 sec) × 32 cycles; No melting curve. Fourth, recorded qPCR Ct values for all samples. Fifth, set threshold to 0.5 – this recommendation was for StepOnePlus System. Note: Typical acceptable Ct values range from 10 to 23.

PCR Amplification of cDNA and Dual Index Addition

First, Index primers were thawed at room temperature until fully melted. Shook to mix and spun in mini-centrifuge for 3 seconds. Stored on ice until use. Second, prepared PCR amplification reaction mix according to Table 34 in fresh 0.2 mL PCR strip-tubes. Kept tubes on ice. Note: If samples are going to be multiplexed during high-throughput sequencing, ensure that all samples to be pooled together have a unique combination of indexing primers.

TABLE 34

PCR amplification reaction mix contents (prepare individually for each sample) –Note - can use traditional Illumina index primers

| Component | Volume (µL) |
|---|---|
| Ligated cDNA | 16 |
| 501 Index Primer | 2 |
| 701 Index Primer | 2 |
| PCR mix | 20 |
| Total: | 40 |

Third, pipetted mix to combine. Fourth, spun samples in mini-centrifuge for 3 seconds to draw all liquid to the bottom of the tube. Fifth, kept samples on ice. Sixth, referred to Ct values recorded to calculate the appropriate number of cycles for each sample. Used formula to calculate N = Ct - 6, where N is the number of cycles performed using the second (two-step) cycling conditions: N + 6 = Total cycles = Ct. Note: e.g. If Ct = 13.1, then N = 7 and Total number of PCR cycles equal 13 (6+7).

Seventh, PCR for the specific number of cycles calculated for each sample was ran according to the PCR program shown in Table 35.

TABLE 35

| PCR Amplification program | | |
|---|---|---|
| Temperature | Time | Cycles |
| 98° C. | 30 seconds | |
| 98° C. | 15 seconds | 6 |
| 70° C. | 30 seconds | |
| 72° C. | 40 seconds | |
| Extra N cycles (N = Ct value – 9) | | |
| 98° C. | 15 seconds | N* |
| 72° C. | 45 seconds | |
| 72° C. | 1 minute | |
| 4° C. | ∞ | |
| Total number of PCR cycles | | 6+N |

*N should be ≥ 1 and < 14.

Eighth, samples were immediately on ice to cool following PCR amplification.

AMPure Library PCR Product Cleanup

Preparative Note: Allowed AMPure XP beads to equilibrate at room temperature for 5 minutes.

First, AMPure XP beads were manually shook or vortexed to resuspend the sample until homogeneous. Second, added 60 µL of AMPure XP beads into each 40 µL PCR reaction. Third, pipetted to mix until sample is homogeneous. Fourth, incubated at room temperature for 10 minutes, with pipette mixing every 5 minutes. Fifth, placed strip-tube on 96-well magnet and allowed to incubate for 1 minute or until separation was complete and liquid was transparent. Sixth, carefully aspirated and discarded supernatant without disturbing beads. Seventh, added 150 µL of 80% EtOH without disturbing beads. Eighth, moved samples to different positions on magnet to wash thoroughly. Ninth, carefully added an additional 150 µL of 80% EtOH. Tenth, incubated on magnet for 30 seconds or until separation was complete and supernatant was transparent. Eleventh, carefully aspirated and discarded supernatant. Twelfth, repeated steps 7-11 for a total of two washes. Thirteenth, spun capped samples in mini-centrifuge for 3 seconds to draw all liquid to the bottom of the tube. Fourteenth, placed tube back on 96-well magnet. Fifteenth, incubated on magnet for 30 seconds or until separation was complete and supernatant was transparent. Sixteenth, while on magnet, aspirated and discarded all residual liquid without disturbing beads. Seventeenth, allowed beads to air dry for 5 minutes or until beads no longer appeared wet and shiny. Eighteenth, once completely dry, carefully removed tubes from magnet. Nineteenth, added 20 µL Molecular Biology Grade Water to each sample. Twentieth, pipetted mix until sample is homogeneous. Twenty-first, incubated for 5 minutes at room temperature. Twenty-second, transferred the 20 µL of eluted sample to new strip-tube. Twenty-third, analyze library length and concentration via Agilent Tapestation. Twenty-fourth, if adapter dimer was present, preform an agarose gel extraction for a DNA 200-400 nts in length and retapestation. Twenty-fifth, libraries were sequenced on an Illumina Nextseq 2000. Twenty-sixth, sequencing reads were mapped to the human genome, hg38 using STAR. Twenty-seventh, reads were split into each barcode/RBP computationally using sequences in Table 16 or 17.

Figure 12:
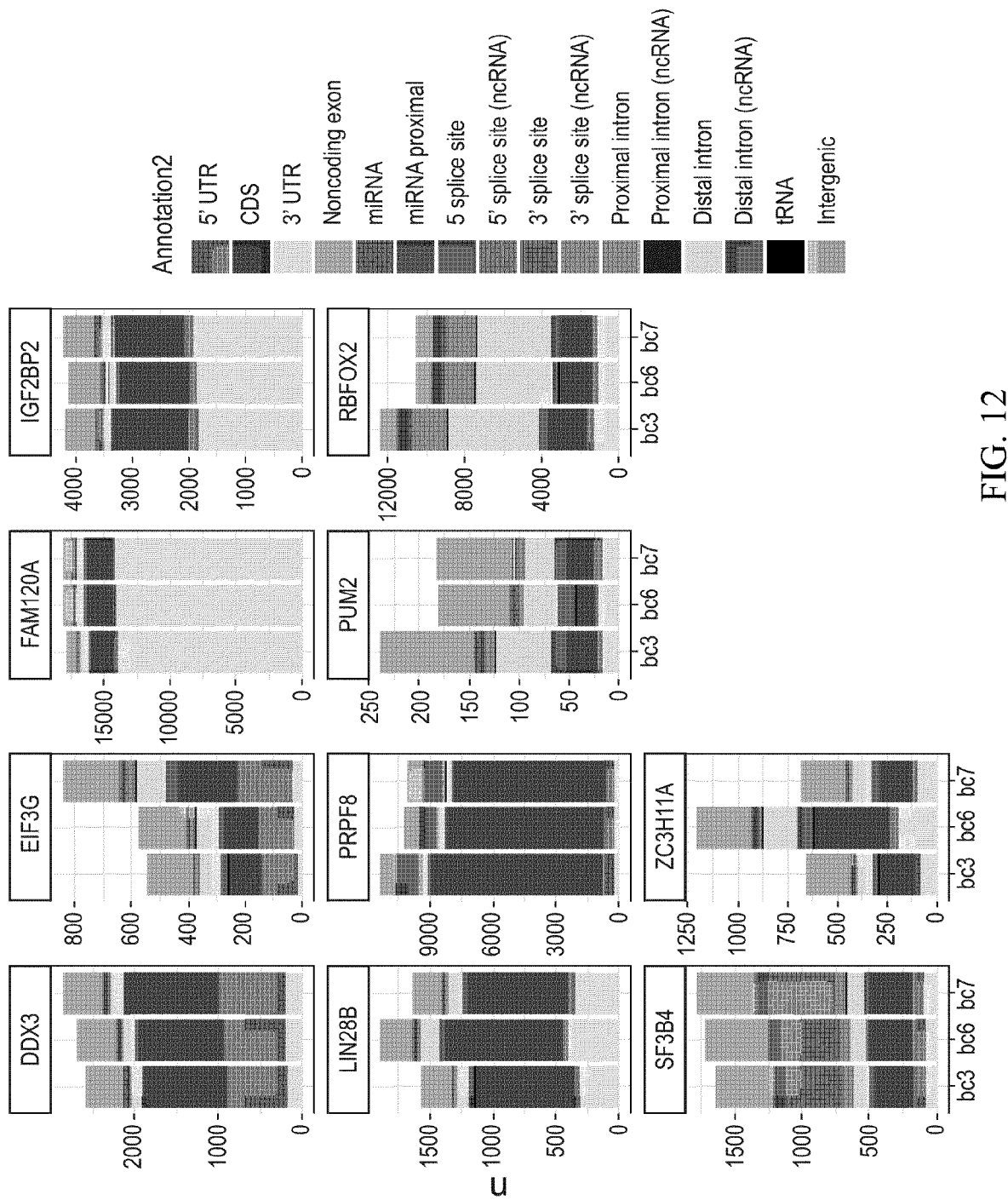
FIG. 12 illustates bar graphs depicting the total number of peaks for each barcode after selective amplification.

FIGS. 11 and 12 illustrate results of the protocol described above. For FIG. 11, three specific barcodes (BC3, 6, and 7 - Columns) were selectively amplified. All ten barcodes were quantified by qPCR (Rows) with Ct values in the table displayed. Amplification resulted in approximately 2 cycle improvements for the target barcode with no changes observed for other barcodes within that sample. For FIG. 12, the libraries amplified in FIG. 11, were sequenced and peaks were called for each barcode. The arrows highlight increased number of peaks detected after selective amplification. The X-axis represent each selective amplification (BC3, 6, and 7) and the Y-axis displays the number of peaks with each box representing a different RBP/Barcode.

What is claimed is:

1. A method of identifying RNA targets of RNA binding proteins, the method comprises:
    contacting an RNA sample with one or more RNA binding proteins and an entity configured to bind the RNA binding protein to form a RNA-protein complex, the entity comprising one or more conjugated proximity oligonucleotides; and
    ligating any RNA targets in the RNA sample to the one or more proximity oligonucleotides with proximity-based ligation to form one or more chimeric RNA molecules.

2. The method of claim 1, wherein the one or more chimeric RNA molecules are amplified by PCR.

3. The method of claim 1, wherein the one or more oligonucleotides conjugated entities contain specific sequences capable of identifying the RNA-protein complex.

4. The method of claim 3, wherein the one or more oligonucleotides conjugated entities contains less than ten different sequences.

5. The method of claim 3, wherein the one or more oligonucleotides conjugated entities contains ten or more different sequences.

6. The method of claim 1, wherein the one or more oligonucleotides conjugated entities contains a randomized sequence capable of determining if a molecule is unique or a PCR duplicate.

7. The method of claim 1, further comprising isolating the RNA-protein complex.

8. The method of claim 7, further comprising lysing cells prior to isolating the RNA-protein complex.

9. The method of claim 7, wherein isolating the RNA-protein complex is by immunoprecipitation of the RNA-protein complex.

10. The method of claim 1, wherein the one or more oligonucleotides conjugated entities is selected from the group consisting of an antibody, a recombinant Fab, nanobody, aptamer, a bead, or an antibody-coupled magnetic bead.

11. The method of claim 10, wherein the bead is a magnetic bead capable of binding IgG antibodies.

12. The method of claim 1, further comprising generating one or more oligonucleotides conjugated antibodies.

13. The method of claim 1, wherein contacting the RNA sample further comprises crosslinking the RNA-protein complex together by UV light or a chemical crosslink agent.

14. The method of claim 13, wherein the chemical crosslink agent is selected from formaldehyde, formalin, acetaldehyde, prionaldehyde, water-soluble carbomiidides, phenylglyoxal, and UDP-dialdehyde.

15. The method of claim 1, wherein the one or more RNA binding protein is selected from RBFOX2, PUM2, DDX2, FAM120A, ZC3H11A, SF3B4, EIF3G, LIN28B, PRPF8, IG2BP2, YTHDF2, and U2AF2.

16. The method of claim 1, wherein the oligonucleotides are conjugated to the entity using an amine or thiol reactive probe.

17. The method of claim 16, wherein the amine or thiol reactive probe enable oligonucleotide conjugation via a click chemistry reaction.

18. The method of claim 17, wherein the click chemistry reaction is copper catalyzed alkyne azide cycloaddition, strained promoted alkyne azide cycloaddition, or inverse electron demand Diels-Alder.

19. The method of claim 1, further comprising amplifying the one or more chimeric RNA molecules to produce an amplified product.

20. The method of claim 1, further comprising identifying a computationally chimeric RNA molecule of interest.

* * * * *